United States Patent
Chung et al.

(10) Patent No.: US 9,303,064 B2
(45) Date of Patent: Apr. 5, 2016

(54) PEPTIDE INHIBITING MATRIX METALLOPROTEANASES ACTIVITY AND USE THEREOF

(75) Inventors: Young Ji Chung, Gyeonggi-do (KR); Eun Mi Kim, Gyeonggi-do (KR)

(73) Assignee: CAREGEN CO., LTD., Gyeonggi-do (KR)

( * ) Notice: Subject to any disclaimer, the term of this patent is extended or adjusted under 35 U.S.C. 154(b) by 0 days.

(21) Appl. No.: 14/343,850

(22) PCT Filed: Nov. 2, 2011

(86) PCT No.: PCT/KR2011/008272
§ 371 (c)(1),
(2), (4) Date: Jun. 9, 2014

(87) PCT Pub. No.: WO2013/035931
PCT Pub. Date: Mar. 14, 2013

(65) Prior Publication Data
US 2014/0328782 A1    Nov. 6, 2014

(30) Foreign Application Priority Data

Sep. 9, 2011   (KR) .................. 10-2011-0091923

(51) Int. Cl.
| | | |
|---|---|---|
| A61K 38/00 | (2006.01) | |
| A61K 38/08 | (2006.01) | |
| A61K 8/64 | (2006.01) | |
| A61K 31/728 | (2006.01) | |
| A61Q 19/00 | (2006.01) | |
| A61Q 19/02 | (2006.01) | |
| A61Q 19/06 | (2006.01) | |
| A61Q 19/08 | (2006.01) | |
| C07K 7/06 | (2006.01) | |

(52) U.S. Cl.
CPC ... *C07K 7/06* (2013.01); *A61K 8/64* (2013.01); *A61K 31/728* (2013.01); *A61K 38/08* (2013.01); *A61Q 19/00* (2013.01); *A61Q 19/02* (2013.01); *A61Q 19/06* (2013.01); *A61Q 19/08* (2013.01); *A61K 38/00* (2013.01); *A61K 2800/782* (2013.01)

(58) Field of Classification Search
CPC ........... A61K 2800/782; A61K 31/728; A61K 38/00; A61K 38/08; A61K 8/64; A61Q 19/00; A61Q 19/02; A61Q 19/06; A61Q 19/08; C07K 7/06
USPC .................. 424/62; 514/18.6, 18.8, 19.3, 4.8; 530/328
See application file for complete search history.

(56) References Cited

U.S. PATENT DOCUMENTS

| | | | |
|---|---|---|---|
| 6,103,697 A | 8/2000 | Bergstrand et al. | |
| 6,534,635 B1 * | 3/2003 | Miyazaki et al. | 530/402 |
| 6,624,144 B1 | 9/2003 | Koivunen et al. | |
| 7,183,256 B2 * | 2/2007 | Anand-Apte | 514/8.1 |
| 7,371,812 B2 * | 5/2008 | Moses et al. | 530/325 |
| 2003/0194704 A1 * | 10/2003 | Penn et al. | 435/6 |
| 2004/0224398 A1 * | 11/2004 | Anand-Apte | 435/184 |
| 2007/0207967 A1 | 9/2007 | Bjorklund et al. | |

FOREIGN PATENT DOCUMENTS

| | | |
|---|---|---|
| JP | 2006-117592 A | 5/2006 |
| JP | 2009-051790 A | 3/2009 |
| KR | 10-2007-0121461 A | 12/2007 |

OTHER PUBLICATIONS

International Search Report for PCT/KR2011/008272.

* cited by examiner

*Primary Examiner* — Julie Ha
(74) *Attorney, Agent, or Firm* — Vorys, Sater, Seymour & Pease LLP

(57) ABSTRACT

A peptide inhibiting a matrix metalloproteinase activity, thereby improving the condition of skin and a composition containing the peptide is described, where the peptide comprises an amino acid sequence represented by the formula: $X_{aa1}$-$X_{aa2}$-Pro-Cys-$X_{aa3}$-$X_{aa4}$-$X_{aa5}$-Ser-$X_{aa6}$ and has excellent bioactivities of inhibiting the activity of hyaluronic acid degrading enzymes, adipogenesis in fat cells, angiogenesis, and the like, thereby being useful for the treatment of various disease such as obesity, cancer, and inflammation.

13 Claims, 21 Drawing Sheets

| Experimental material | area | (%) control |
|---|---|---|
| Negative control | 1898694 | 100 |
| Positive control | 1217263 | 64.1 |
| SEQ ID NO:1 | 1556981 | 92.0 |
| SEQ ID NO:2 | 1583446 | 93.4 |
| SEQ ID NO:3 | 1488778 | 88.4 |

| Experimental material | area | (%) control |
|---|---|---|
| Negative control | 6539383 | 100 |
| Positive control | 3116642 | 47.7 |
| SEQ ID NO:1 | 6417999 | 98.1 |
| SEQ ID NO:2 | 6678659 | 102.1 |
| SEQ ID NO:3 | 6932365 | 106.0 |

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: CG-Formade

<400> SEQUENCE: 1

```
Ser Ile Pro Cys Lys Leu Gln Ser Gly
1               5

<210> SEQ ID NO 2
<211> LENGTH: 9
<212> TYPE: PRT
<213> ORGANISM: Artificial Sequence
<220> FEATURE:
<223> OTHER INFORMATION: CG-Seperin

<400> SEQUENCE: 2

Met Ile Pro Cys Tyr Ile Ser Ser Pro
1               5

<210> SEQ ID NO 3
<211> LENGTH: 9
<212> TYPE: PRT
<213> ORGANISM: Artificial Sequence
<220> FEATURE:
<223> OTHER INFORMATION: CG-Recollin

<400> SEQUENCE: 3

Tyr Leu Pro Cys Phe Val Thr Ser Lys
1               5
```

PEPTIDE INHIBITING MATRIX METALLOPROTEANASES ACTIVITY AND USE THEREOF

CROSS REFERENCE TO RELATED APPLICATIONS AND CLAIM OF PRIORITY

This patent application is a National Phase application under 35 U.S.C. §371 of International Application No. PCT/KR2011/008272filed 02 Nov. 2011, which claims priority to Korean Patent Application No. 10-2011-0091923, filed 9 Sep. 2011, entire contents of which are incorporated herein by reference

BACKGROUND OF THE INVENTION

1. Field of the Invention

The present invention relates to a peptide inhibiting a matrix metalloproteanases activity and use thereof.

2. Description of the Related Art

Matrix metalloproteinase (MMP) is a group of endopeptidase capable of degrading macro-biomolecule such as collagen, proteoglycan and gelatin. And MMP is classed as collagenase, gelatinase, stromelysin and Membrane-type MMP. All of MMP is expressed in form of proenzyme, and activated by cutting its portion out (Bond, J. S., et al., *Int. J. Biochem.*, 75, 565-574 (1985); Chen, J. M., Chen, W. T., *Cell*, 48, 193-203 (1987); Harris, E. D. et al., *Coll Rel Res*, 4, 493-512 (1984)).

Collagenase acts on triple-helix form epileptic collagen, gelatin, and the like, and is known to three kinds of collagenase, such as fibroblast collagenase, neutrophilic leukocyte collagenase and collagenase-3. In addition, It has been reported that collagenase cuts off type I, II and III of collagen fibrils (Goldberg, G. I., et al, *J. Biol. Chem.*, 261, 6600-6605 (1986); Fini, M. E., et al., *Biochemistry*, 26, 6155-6165 (1987)). Furthermore, it has been reported that these three collagenases have at least about 50% sequence identity (Borkakoti, et al., *Nature Struct. Biol.*, 1, 106-110 (1994); EMBO, J., 13, 1263-1269 (1994)).

MMP falls into a propeptide domain, a catalytic domain and a c-terminal domain. MMP is made of cryptoplasmic form and secreted, and activated by cutting 80 amino acids of N-terminal propeptide domain out and removing cysteine residue of domain having PRCGVPD sequences (Van Wart, H. E. et al., *Proc. Nati. Acad. Sci. USA*, 87, 5578-5582 (1990)). It has been reported that activity of the activated MMP is inhibited by coupling with tissue inhibitor of matrix metalloproteinase (TIMP), the coupling is regulated by the catalytic domain (Murphy, et al., *J. Niol. Chem.*, 267, 9612-9618 (1992)). Various forms of MMP have substrate specificity, and is expressed in metabolic process when need to degrade extracellular matrix or structure of collagen in normal tissues. MMP-associated disorder is atherosclerosis, inflammatory disease of the central nervous system, Alzheimer's disease, skin aging, rheumatoid arthritis, osteoarthritis, corneal ulcers, bone disease, albuminuria, abdominal aneurysm disease, degenerative cartilage loss due to traumatic joint injuries, demyelinating disease of central nervous system, cirrhosis, glomerular disease, Preterm premature rupture of membranes, inflammatory bowel disease, periodontal disease, age-related macular degeneration, diabetic retinopathy, proliferative vitreoretinopathy cardiomyopathy, immature retinopathy, keratoconus, Sjogren's syndrome, myopia, eye tumors, corneal transplant rejection, angiogenesis, cancer invasion and metastasis, and the like. As the disease progressed, the extracellular matrix of articular cartilage is destructed, though autoimmune disorder is cause of rheumatoid arthritis and osteoarthritis. Stromelysin is recognized as a major enzyme at these arthritis and joint trauma and plays an important role in conversion procollagenase into activated collagenase. Therefore, inhibition of MMP activity blocks progression of arthritis, and it has been reported that the MMP is derived from penetrating leukocyte, fibroblast or external microorganism.

Also, collagenase secreted by stimulation of inflammatory mediator and bacteria generate gingival retraction by degrading collagen which is substrate of periodontal tissue, and cause periodontal disease by progression of that. Activity of fibroblast collagenase and stromelysin separated from inflamed gum is shown, and it is revealed that a level of enzyme and observed gingivitis are correlated (Overall, C. M. et al., *J. Periodontal Res*. 22, 81-88(1987)).

MMP is related to pathogenesis of a central nerve system. It is assumed that MMP destroys myelin and blood-brain barrier by inflowing inflammatory mononuclear cell into central nerve, and it is involved in accumulation of amyloid beta protein in Alzheimer's disease (Yong, V W, et al., *Trends Neurosci* 21(2), 75-80 (1998)). Also, it has been reported that concentration of MMP is higher in Alzheimer's diseased brain than in normal brain (Leake A, Morris C M, & Whateley *J. Neurosci Leu* 291(3), 201-3(2000), and it has been reported that level of gelatinase in cerebrospinal fluid is related to multiple sclerosis and other nerve disease and contributes accumulation of amyloid beta protein after degrading it (Backstrom J R, et al., *J neurosci* 16(24), 7910-9 (1996)).

In addition, because MMP induces skin aging, inhibition of MMP anticipates treatment and prevention of wrinkle; furthermore MMP facilitates angiogenesis and cancer invasion and metastasis through basilar membrane degradation. Therefore, there is a need for the development of drugs which is capable of inhibiting MMP because MMP not only plays an important role in cancer invasion and metastasis through basilar membrane degradation but also mediates various diseases. However, there is a need for the development of nontoxic agents as MMP activity inhibitor because the inhibitor can use in ideal medicine only if it can be safely with long-term use.

Furthermore, study on MMP inhibitors has been actively conducted for effective treatment of various MMP-mediated diseases, and the development of MMP inhibitors is used in treatment of various diseases effectively.

Throughout this application, various patents and publications are referenced, and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventors have made intensive researches to develop excellent peptides inhibiting a matrix metalloproteanases activity and have screened peptides after synthesizing various types of peptide. As a result, The present inventors have selected peptides which are superior not only in biological activity such as effects of inhibition of collagen degradation, inhibition of cell death by oxidative stress, inhibition of a matrix metalloproteanase 2 activity and inhibition of hyaluronic acid degradation, but also in skin penetration ratio.

Accordingly, it is one object of this invention to provide a peptide comprising the amino acid sequence represented by the following formula 1:

$$X_{aa1}\text{-}X_{aa2}\text{-}Pro\text{-}Cys\text{-}X_{aa3}\text{-}X_{aa4}\text{-}X_{aa5}\text{-}Ser\text{-}X_{aa6} \qquad (1)$$

It is another object of this invention to provide a cosmetic composition for improving skin conditions, comprising the peptide as an active ingredient.

It is still another object of this invention to provide a pharmaceutical composition for improving skin conditions, comprising the peptide as an active ingredient.

It is still another object of this invention to provide a skin filler, comprising the peptide and hyaluronic acid.

It is still another object of this invention to provide a pharmaceutical composition for preventing or treating obesity, comprising the peptide as an active ingredient.

It is still another object of this invention to provide a pharmaceutical composition for preventing or treating inflammation, comprising the peptide as an active ingredient.

It is still another object of this invention to provide a pharmaceutical composition for preventing or treating cancer, comprising the peptide as an active ingredient.

It is still another object of this invention to provide a pharmaceutical composition for preventing or treating a MMP-activity related disorder, comprising the peptide as an active ingredient.

Other objects and advantages of the present invention will become apparent from the following detailed description together with the appended claims and drawings.

In one aspect of this invention, there is provided a peptide comprising the amino acid sequence represented by the following formula 1:

$$X_{aa1}\text{-}X_{aa2}\text{-}Pro\text{-}Cys\text{-}X_{aa3}\text{-}X_{aa4}\text{-}X_{aa5}\text{-}Ser\text{-}X_{aa6} \tag{1}$$

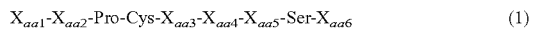

wherein $X_{aa1}$ represents Ser, Met, Tyr, Gly, Ala, Val, Leu or Ile, $X_{aa2}$ represents Ile, Leu, Val, Ser, Met, Tyr, Gly or Ala, $X_{aa3}$ represents Lys, Tyr or Phe, $X_{aa4}$ represents Leu, Ile, Val, Ser, Met, Tyr, Gly or Ala, $X_{aa5}$ represents Gln, Ser or Thr, $X_{aa6}$ represents Gly, Pro or Lys.

The present inventors have made intensive researches to develop excellent peptides inhibiting a matrix metalloproteanases activity and have screened peptides after synthesizing various types of peptide. As a result, we have selected peptides which are superior not only in biological activity such as effects of inhibition of collagen degradation, inhibition of cell death by oxidative stress, inhibition of a matrix metalloproteanase 2 activity and inhibition of hyaluronic acid degradation, but also in skin penetration ratio.

More specifically, the present inventors synthesized candidate peptides by selecting a virtual portion of capable of binding to a matrix metalloproteinase which is already known through Homology Search using a computer and docking methods, and then optimizing an amino acid sequence of the predicted portion. Afterwards the candidate peptides were synthesized by performing solid-phase synthesis using chloro trityl chloride resin and Fmoc-amino acids, the present inventors isolated wanted peptides by removing Fmoc-protecting group from the resin using trifluroacetic acid. After going through purification and analysis course and checking of contents and purity on the synthesized peptides, the peptides of the present invention are selected by screening the peptides having the most excellent bioactivity through various biological tests.

The peptide according to the present invention, the $X_{aa1}$ represents Ser, Met or Tyr, the $X_{aa2}$ represents Ile or Leu, the $X_{aa3}$ represents Lys, Tyr or Phe, the $X_{aa4}$ represents Leu, Ile or Val, the $X_{aa5}$ represents Gln, Ser or Thr, the $X_{aa6}$ represents Gly, Pro or Lys. According to a certain embodiment, the peptide is selected from the group consisting of amino acid sequences of SEQ ID NO:1-3.

The term used herein "peptide" refers to a linear molecule formed by linking between amino acid residues through peptide bonds. The peptides of the present invention may be prepared by conventional chemical synthesis processes known to one of skill in the art, in particular, solid-phase synthesis techniques (Merrifield, *J. Amer. Chem. Soc.* 85: 2149-54 (1963); Stewart, et al., *Solid Phase Peptide Synthesis,* 2nd. ed., Pierce Chem. Co.: Rockford, 111 (1984)).

The term used herein "peptide" refers to a linear molecule formed by linking amino acid residues through peptide bonds. The peptides of the invention may be prepared by conventional chemical synthesis processes known to one of skill in the art, in particular, solid-phase synthesis techniques (Merrifield, *J. Amer. Chem. Soc.,* 85: 2149-54 (1963); Stewart, et al., *Solid Phase Peptide Synthesis,* 2nd. ed., Pierce Chem. Co.: Rockford, 111 (1984)).

The peptide of the present invention is selected a portion of amino acid sequences and induce modifications at N-terminal or C-terminal for improving its activity. Its modification enables to have much longer half-life when the peptide is administered into a living system.

In addition, the peptides of this invention has at their C-terminal a protection group selected from the group consisting of hydroxyl group (—OH), amino group (—NH$_2$) and azide group (—NHNH$_2$), and at their N-terminal a protection group selected from the group consisting of acetyl group, fluorenyl methoxy carbonyl group, formyl group, palmitoyl group, myristyl group, stearyl group and polyethylene glycol (PEG).

The modifications of peptides described above greatly increase the stability of the peptides of this invention. The term used herein "stability" refers to in vivo stability and storage stability (e.g., storage stability at room temperature) as well. The protection group described above protects the peptides from the attack of protease of a living system.

According to a certain embodiment, the peptide of the present invention facilitates cell growth in human primary dermal fibroblast and fibroblast, and inhibits cell death by oxidative stress. Also, after inducing cell death by irradiating UV directly to cell, the treatment of the peptide of the present invention inhibits cell death. In addition, the peptide of the present invention not only directly inhibits the matrix metalloproteanase activity, but also inhibits degradation of collagen by matrix metalloproteanases. Furthermore, the peptide of the present invention exhibits an excellent efficacy of inhibiting melanosome transfer which is important to skin whitening. These results means that the peptide of the present invention has an excellent efficacy of improving the condition.

In another aspect of this invention, there is provided a cosmetic composition for improving skin conditions, comprising the peptide of the present invention as an active ingredient.

In still another aspect of this invention there is provided a method for improving skin conditions, comprising administering to a subject a composition containing the peptide of the present invention as an active ingredient.

According to a certain embodiment, the improvement of skin conditions of the present invention is the improvement in wrinkle or skin elasticity, prevention of skin aging, improvement in skin moisture, removal of wound, regeneration of skin or skin whitening.

In still another aspect of this invention there is provided a pharmaceutical composition for improving skin conditions, comprising the peptide of the present invention as an active ingredient.

According to a certain embodiment, the improvement of skin conditions of the present invention is removal of wound or regeneration.

In still another aspect of this invention there is provided a skin filler comprising the peptide of the present invention and hyaluronic acid.

In still another aspect of this invention there is provided a method for filling a skin, comprising administering to a subject the peptide of the present invention and hyaluronic acid.

The peptide of the present invention exhibits excellent efficacy of improving the long-term safety by inhibiting the hyaluronate lyase activity in case of application of the peptide to filler products.

In still another aspect of this invention there is provided a pharmaceutical composition for preventing or treating obesity, comprising the peptide of the present invention as an active ingredient.

In still another aspect of this invention there is provided a method for preventing or treating obesity, comprising administering to a subject a composition containing the peptide of the present invention as an active ingredient.

The peptide of the invention has excellent activities of inhibiting adipogenesis when the peptide treats to adipocytes, thereby being useful for the prevention or treatment of obesity.

In still another aspect of this invention there is provided a pharmaceutical composition for preventing or treating inflammation, comprising the peptide of the present invention as an active ingredient.

In still another aspect of this invention there is provided a method for preventing or treating inflammation, comprising administering to a subject a composition containing the peptide of the present invention as an active ingredient.

The peptide of the present invention exhibits excellent efficacy of anti-inflammation inhibiting the expression of inflammation-related proteins in case of the treatment of the peptide of the present invention to periodontal cells.

In still another aspect of this invention there is provided a pharmaceutical composition for preventing or treating cancer, comprising the peptide of the present invention as an active ingredient.

In still another aspect of this invention there is provided a method for preventing or treating cancer, comprising administering to a subject a composition containing the peptide of the present invention as an active ingredient.

The peptide of the present invention inhibits angiogenesis by suppressing tube formation in vascular endothelial cell, thereby being applicable to treatment of various cancers.

In still another aspect of this invention there is provided a pharmaceutical composition for preventing or treating a MMP-activity related disorder, comprising the peptide of the prevent invention as an active ingredient, wherein the MMP-activity related disorder comprises arthritis, diabetic retinopathy, hypertrophic cicatrix, psoriasis, ulcer of mucous membrane and epithelial tissue, inflammation by autoimmune response; lupus, autoimmune neuropathy, destruction of myocyte as basilar membrane degradation related disorder; glaucoma or excessive angiogenesis.

In still another aspect of this invention there is provided a method for preventing or treating a MMP-activity related disorder, comprising administering to a subject a composition containing the peptide of the present invention as an active ingredient, wherein the MMP-activity related disorder comprises arthritis, diabetic retinopathy, hypertrophic cicatrix, psoriasis, ulcer of mucous membrane and epithelial tissue, inflammation by autoimmune response; lupus, autoimmune neuropathy, destruction of myocyte as basilar membrane degradation related disorder; glaucoma or excessive angiogenesis.

The peptide of the present invention has various bioactivities of inhibiting the activity of matrix metalloproteinase (MMP), collagen degradation, hyaluronic acid degradation, formation of lipid in adipocyte cell and angiogenesis, thereby being useful for the treatment of related diseases.

In addition, skin permeability of the peptide of the present invention is excellent due to molecular-weight of the peptide is lower than that of other proteins. So, the compositions comprising the peptide of the present invention effectively improve conditions of skin in case of application of the peptide to skin topically.

Therefore, the peptide of the invention can be advantageously applied to drugs and cosmetics and the present composition may be prepared as a pharmaceutical or cosmetic composition.

According to a preferable embodiment, the composition is a pharmaceutical composition comprising (a) a pharmaceutically effective amount of the peptides of the present invention; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, subcutaneous, intramuscular, intraperitoneal, local or transdermal administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 μg.

According to the conventional techniques known to those skilled in the art, the pharmaceutical composition according to the present invention may be formulated with pharmaceutically acceptable carrier and/or vehicle as described above, finally providing several forms such as a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferable embodiment, the composition is a cosmetic composition comprising (a) a cosmetically effective amount of the peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc or zinc oxide.

In the formulation of powder or spray, it may comprise lactose, talc, silica, aluminum hydroxide, calcium silicate or polyamide powder. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents such as ethoxylated isostearyl alcohols, polyoxyethylene sorbitol esters and poly oxyethylene sorbitan esters, microcrystalline cellulose, aluminum metahydroxide, bentonite, agar or tragacanth.

The formulation of cleansing compositions with surfactant may comprise aliphatic alcohol sulfate, aliphatic alcohol ether sulfate, sulfosuccinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives or ethoxylated glycerol fatty acid ester.

Furthermore, the cosmetic compositions of this invention may contain auxiliaries as well as peptides as active ingredients and carriers. The non-limiting examples of auxiliaries include antioxidants, stabilizers, solubilizers, vitamins, colorants and odor improvers.

The features and advantages of the present invention will be summarized as follows:

(a) The peptide of the present invention inhibiting a matrix metalloproteinase activity exhibits an excellent efficacy of improving the condition of skin by directly inhibiting the matrix metalloproteinase activity;

(b) The composition containing the peptide of the present invention has excellent bioactivities of inhibiting the activity of hyaluronic acid degrading enzymes, adipogenesis in fat cells, angiogenesis, and the like, thereby being useful for the treatment of various disease such as anti-obesity, anti-cancer, anti-inflammation;

(c) the peptide of the present invention has excellent skin permeability due to the small size of the peptide;

(d) the outstanding activity and stability of the present peptide described above may be greatly advantageous in application to pharmaceutical compositions, quasi-drugs and cosmetics.

Figure 1A:
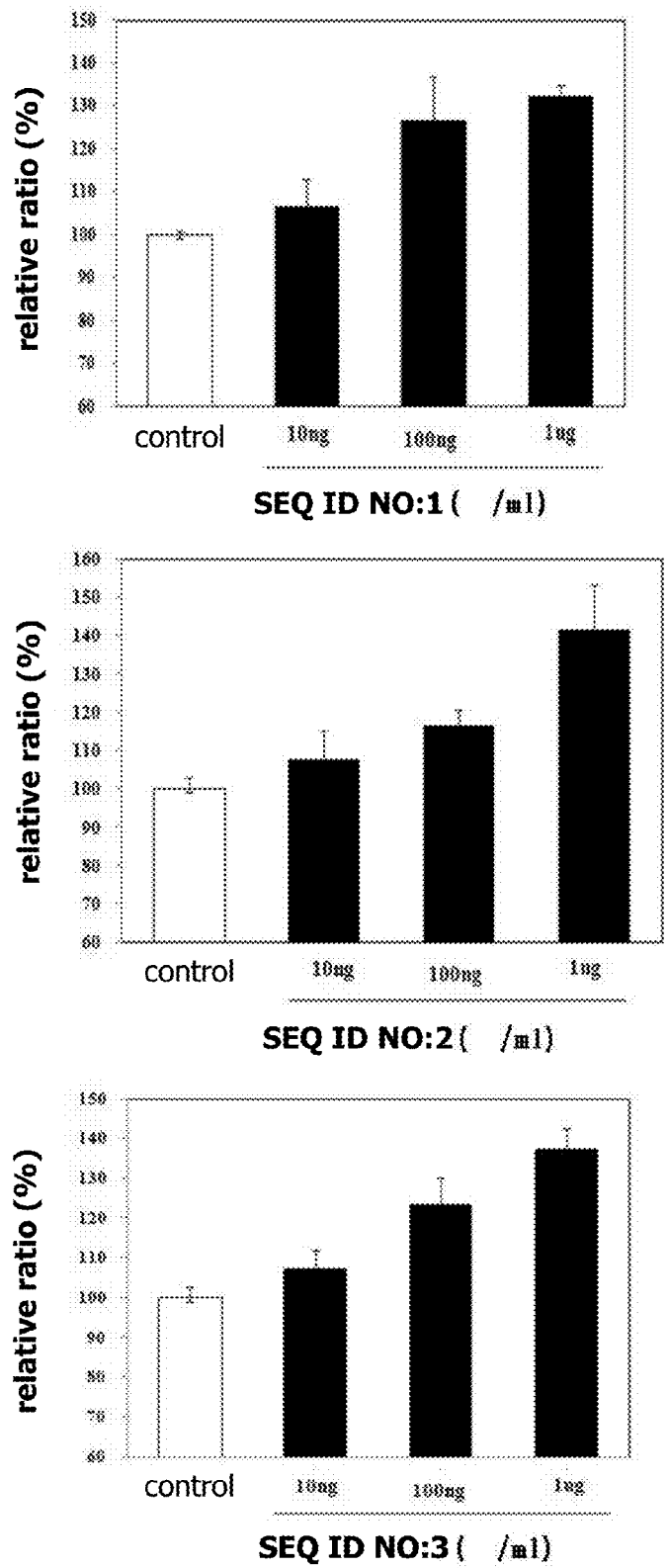
FIG. 1a is a graph demonstrating effects on cell growth of human primary dermal fibroblasts after treating the peptides of the present invention by concentration.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Synthesis of SIPCKLQSG (SEQ ID NO:1)

700 mg of chloro trityl chloride resin (CTL resin, Nova Biochem Cat No. 01-64-0021) introduced into a reactor were added 10 ml of methylene chloride (MC) and agitated for 3 min. After removing solution, 10 ml of dimethylformamide (DMF) were added to the resultant and then agitation was carried out for 3 min, after which the solvent was removed. Ten ml of dichloromethane (DCM) solution were added to the reactor and 200 mmole of Fmoc-Gly-OH (Bachem, Swiss) and 400 mmole of diisopropyl ethylamine (DIEA) were then added to the reactor, after which the mixture was dissolved by agitation and reaction was then undertaken with agitating for 1 hr. After reaction, the resultant was washed and reacted for 10 min in methanol and DIEA (2:1) dissolved in DCM, followed by washing with excess DCM/DMF (1:1). After the removal of the solvent, 10 ml of DMF were added to the reactor and agitated for 3 min, followed by removing the solvent. Ten ml of a deprotection solution (20% piperidine/DMF) were added to the reactor and agitated for 10 min at room temperature, and solution removal was performed. After adding the same volume of the deprotection solution, the reaction was undertaken for 10 min and solution was removed, followed by washing sequentially with DMF (twice), MC (once) and DMF (once) for 3 min respectively to yield Gly-CTL resins. Ten ml of DMF solution was added to a new reactor and then 200 mmole of Fmoc-Ser(tBu)-OH (Bachem, Swiss), 200 mmole of HoBt and 200 mmole of Bop were added, followed by agitation for solubilization. 400 mmole of DIEA was added to the reactor twice as a fraction and agitation was carried out for at least 5 min to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution for 5 min to remove unreacted residuals. A small amount of the reacted resin was taken to evaluate extent of reactions by Ninhydrine test. Using the deprotection solution, the deprotection was performed twice in the same manner as described above to yield Ser(tBu)-Gly-CTL resins. After sufficiently washing with DMF and MC, Ninhydrine test was carried out again and then the attachments of amino acids were performed as described below. Based on the selected amino acid sequence, Fmoc-Gln(Trt), Fmoc-Leu, Fmoc-Lys(Boc), Fmoc-Cys(Trt), Fmoc-Pro, Fmoc-Ile and Fmoc-Ser(tBu) were sequentially attached to the resins. After incubating twice with the deprotection solution for 10 min, the Fmoc-protecting group was removed by washing. After performing acetylation for 1 hr with the acetic anhydride, DIEA and HoBt, the prepared peptidyl resins were washed three times sequentially with DMF, MC and methanol, dried under the flow of nitrogen gas, completely dried by vacuum-drying under P2O5 and then reacted with 30 ml of the leaving solution [containing 95% TFA (trifluroacetic acid), 2.5% distilled water, 2.5% thioanisole] for 2 hr at room temperature upon intermittent agitating. The resin was filtered and washed with a small volume of TFA (Trifluoroacetic acid) solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was completely dried under nitrogen atmosphere to provide 0.7 g of unpurified peptide 1 (yield: 93%), NH₂-Ser-Ile-Pro-Cys-Lys-Leu-Gln-Ser-Gly-COOH. The molecular weight of the final product was determined as 932 (theoretical MW 932.12) using a mass analyzer. The other peptides of SEQ ID NO:2 and SEQ ID NO:3 were also synthesized by the process described in the above.

TABLE 1

| SEQ ID NO | Amino acid sequence | Analyzed values (mass analyzer) | |
|---|---|---|---|
| | | Analyzed values | Theoretical values |
| 1 (Peptide-1) | SIPCKLQSG | 932 | 932.12 |
| 2 (Peptide-2) | MIPCYISSP | 1011 | 1010.24 |
| 3 (Peptide-3) | YLPCFVTSK | 1056.3 | 1057.29 |

Experimental Example 1

Effects of Synthetic Peptides on Growth of Human Primary Dermal Fibroblasts

In order to evaluate the peptides prepared in Preparation Examples 1 whether they have similar activities and inhibition activities of growth factor, SRB (Sulforhodamine B; Sigma-Aldrich) colorimetric assay was carried out using human primary dermal fibroblasts according to Rizzino et al. method (Rizzino, et al. Cancer Res., 48: 4266 (1988)).

Human primary dermal fibroblasts were cultured in 250 ml-flasks containing MSCM (Mesenchymal stem cell medium, Gibco, U.S.A) supplemented with 5% FBS (fetal bovine serum) and 1% MSCGS (Mesenchymal Stem Cell Growth Supplement, Science, U.S.A). Cells cultured were treated with 1% trypsin solution to detach cells from the bottom of culture flasks and centrifuged to collect cell pellets. After cells were resuspended in MSCM not containing FBS, its aliquot ($3 \times 10^3$ cells) was added to each well of 96-well plates and cultured under 5% $CO_2$ for 24 hr at 37° C. After 24-hr culture, the medium was changed with a fresh medium not containing serum and cells were incubated with trial piece for standard or the peptides synthesized (10 ng/ml, 100 ng/ml, 1 µg/ml and 10 µg/ml) dissolved in distilled water for 72 hr under the same conditions as described above. After removing supernatants, cells were fixed using ethanol and washed three times with PBS (phosphate buffered saline). After removing washing solution, cells were treated with SRB solution and sufficiently washed with 1% acetic acid. In addition, cells were observed under a microscope to find cell viability and absorbance at 590 nm was measured to analyze survival status of cells.

Figure 1B:
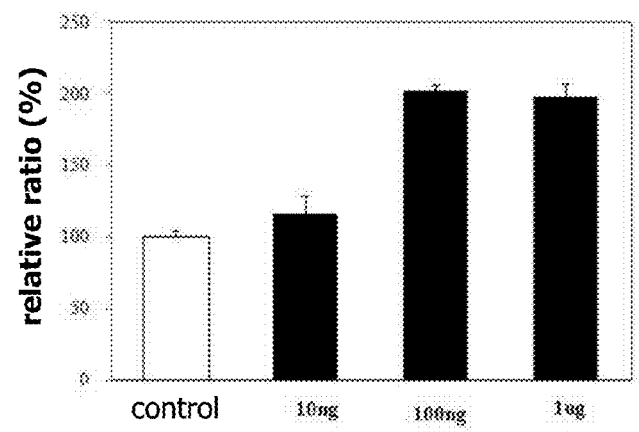
FIG. 1b is a graph demonstrating effects on cell growth of fibroblasts after treating the peptides of the present invention by concentration.
Figure 1B:
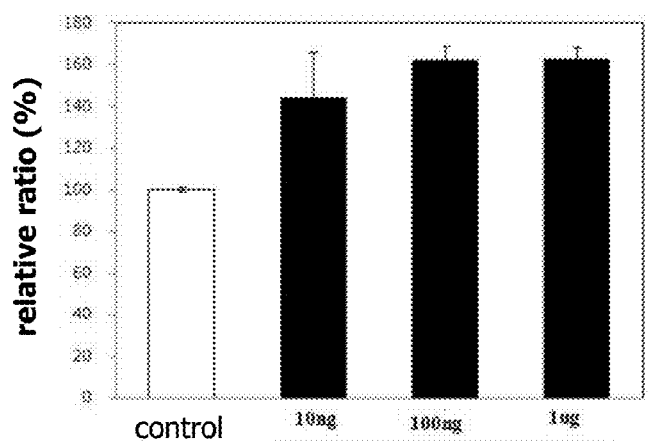
Figure 1B:
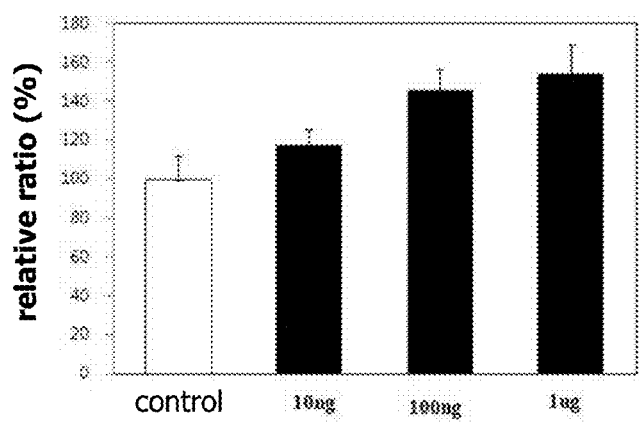
Figure 2:
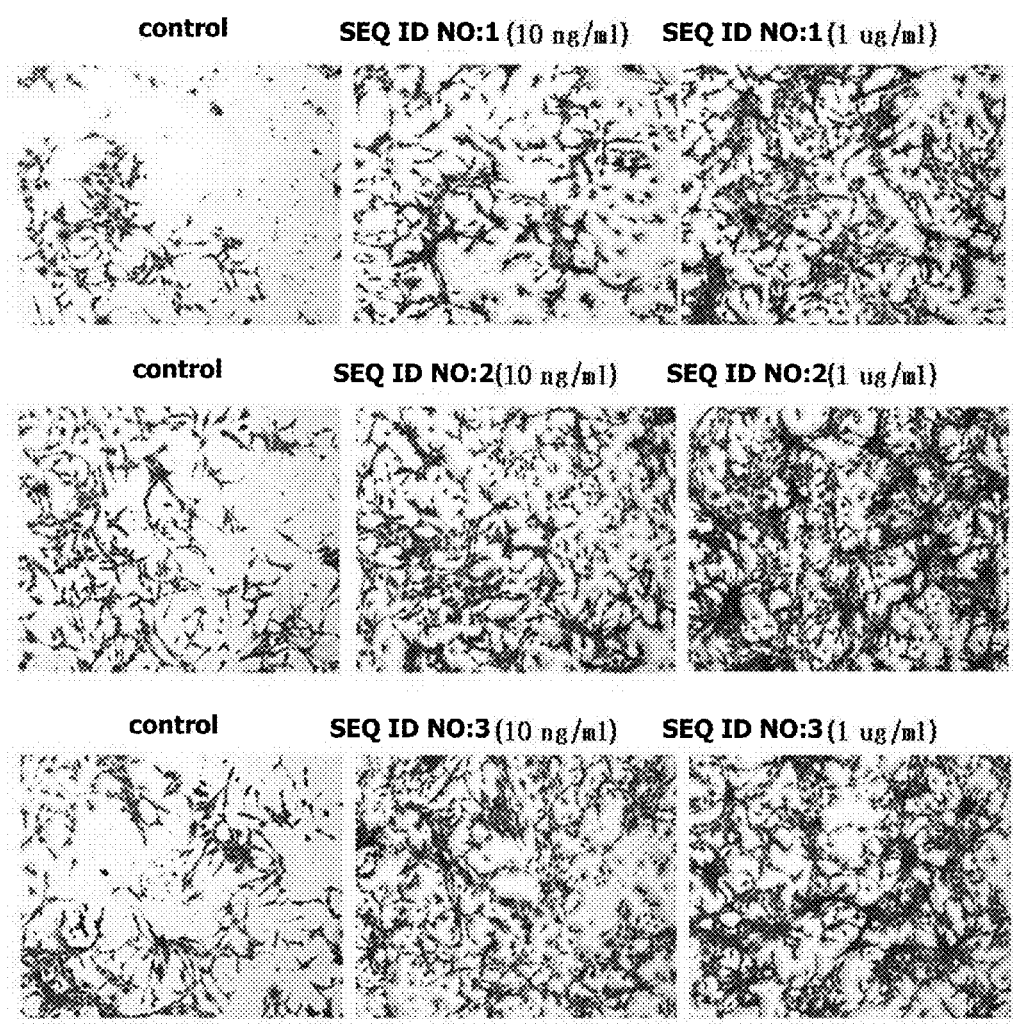
FIG. 2 is a microscope image demonstrating effects on cell growth of fibroblasts after treating the peptides of the present invention.

As shown in FIGS. 1a and 1b, the peptides of this invention (SEQ ID NO:1-3) dramatically facilitate growth of human primary dermal fibroblasts and fibroblasts. In addition, as shown in FIG. 2, it was observed that shape and form of cells are significantly changed due to induction of growth of fibroblasts by the treatment of the peptides (SEQ ID NO:1-3) of this invention.

Experimental Example 2

Inhibitory Effects of Synthetic Peptides on Cell Death by Oxidative Stress

In order to evaluate the peptides prepared in Preparation Examples 1 whether they have inhibition activities of cell death, NIH3T3 which is fibroblast and human primary dermal fibroblasts are tested. The cells were cultured by the same methods as described above, and its aliquot ($3 \times 10^3$ cells) was added to each well of 96-well plates and cultured under 5% $CO_2$ for 24 hr at 37° C. After 24-hr culture, the medium was changed with the same medium not containing serum and cells were treated with 15 µM menadione (Sigma) for applying oxidative stress. After incubating for 48 hr with the peptides synthesized (1 ng/ml, 10 ng/ml, 100 ng/ml and 1000 ng/ml), the cell death was observed. The cells were dyed with SRB solution and absorbance at 590 nm was measured to analyze cell death under the same conditions as described in Experimental Examples 1.

Figure 3A:
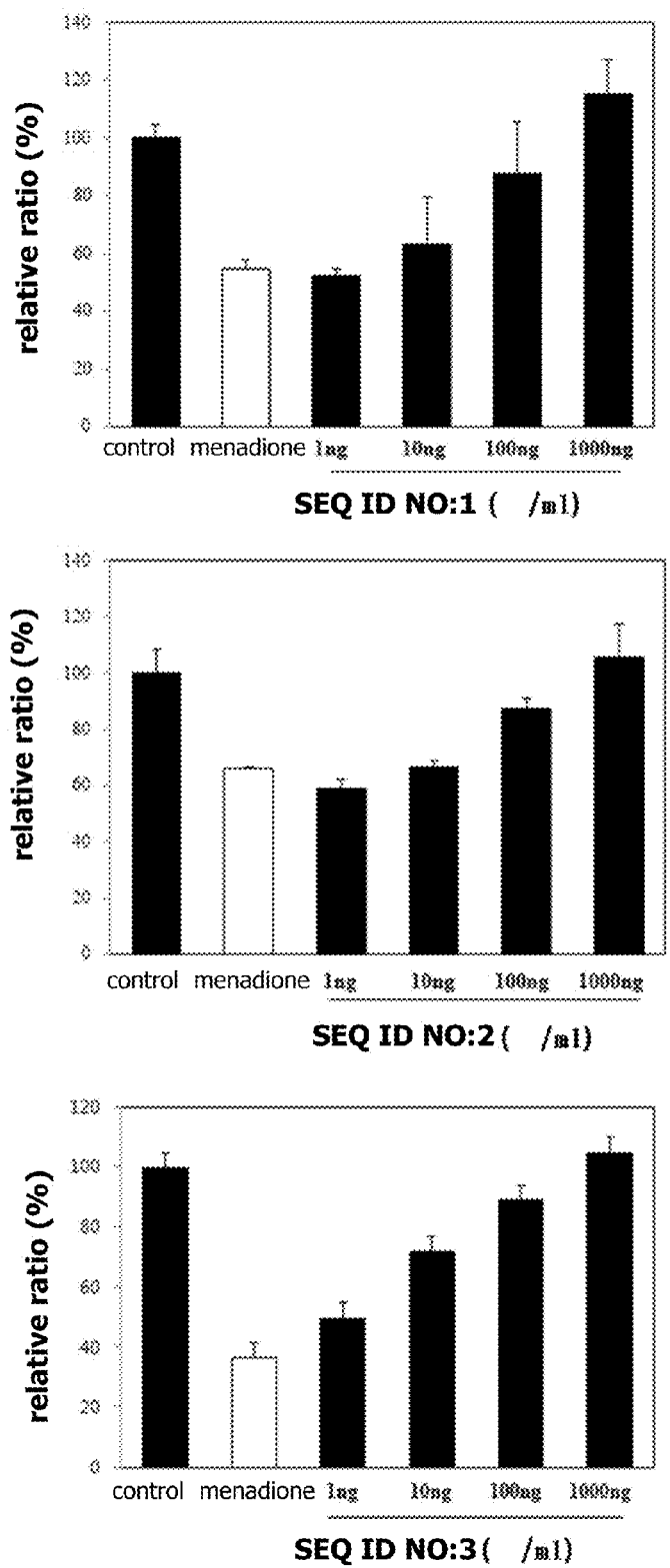
FIG. 3a is a graph demonstrating inhibitory effects of the peptides of the present invention on cell death by oxidative stress.

FIG. 3a represents the data for influence of the peptides (1 ng/ml, 10 ng/ml, 100 ng/ml and 1000 ng/ml) of the present invention on inhibition of cell death after applying oxidative stress by treatment of 15 µM menadione and it shows that the treatment of the peptides inhibits cell death by oxidative stress.

Figure 3B:
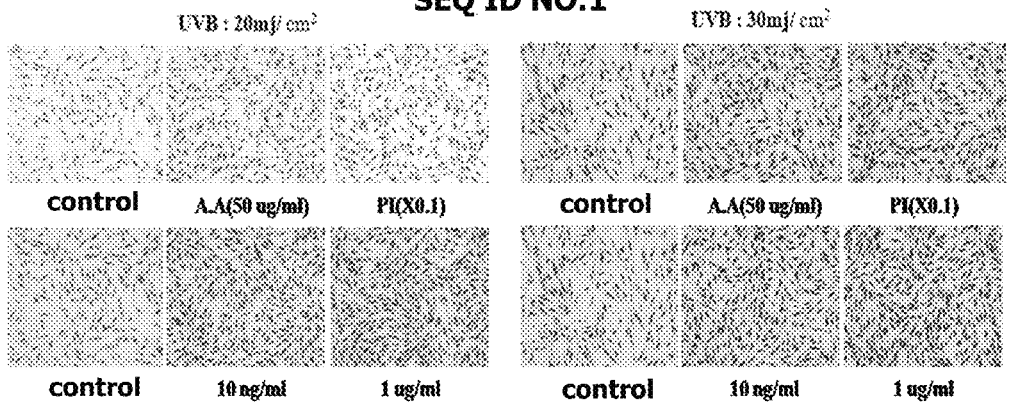
FIG. 3b is a microscope image demonstrating inhibitory effects on cell death of human primary dermal fibroblasts by UV irradiation after treating the peptides of the present invention.
Figure 3B:
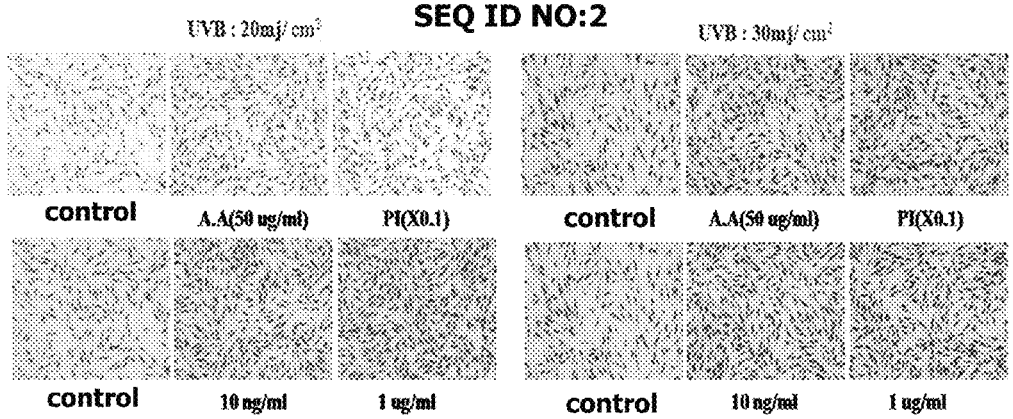
Figure 3B:
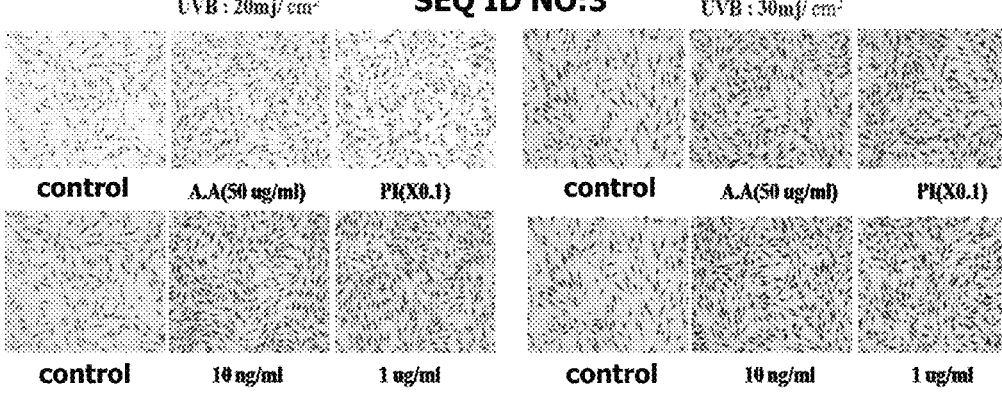

FIG. 3b represents the data for influence of the peptides of the present invention on inhibition of cell death using human primary dermal fibroblasts. After treating the peptides by concentration and irradiating with 20 mJ/cm² UV or 30 mJ/cm² UV, the status of cells were observed. As shown in FIG. 3b, it reveals that cell death is induced in case of irradiation of 20 mJ/cm² UV or 30 mJ/cm² UV, and treatment of the peptides inhibits cell death by UV irradiation by concentration.

Figure 3C:
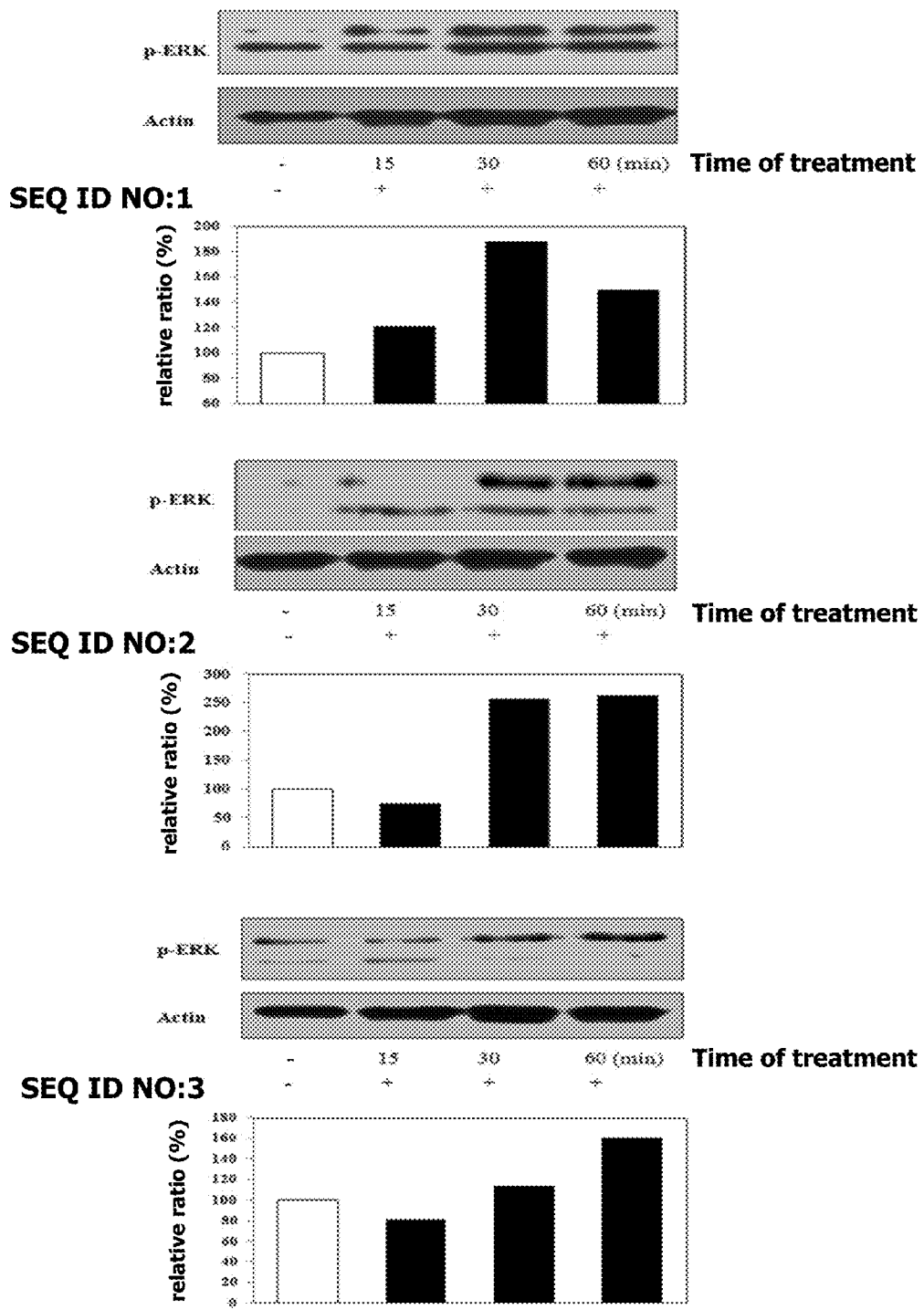
FIG. 3c is an ERK phosphorylation data demonstrating the identical effects with the effects of FIG. 3b

FIG. 3c is results of Western blotting analysis for observing the influence signal of the peptides on inhibition of cell death by oxidative stress. As a result, phosphorylation of ERK (extracellular signal-regulated kinases) facilitates in case of the treatment of the peptides of the present invention by time (15 min, 30 min or 60 min).

Consequentially, FIGS. 3a and 3b show the peptides of the present invention (SEQ ID NO: 1-3) inhibit the cell death induced by oxidative stress in human primary dermal fibroblasts and fibroblast, and that is due to facilitation of ERK phosphorylation by the peptides (FIG. 3c).

Experimental Example 3

Inhibitory Effects of Synthetic Peptides on a Matrix Metalloprotease 2 Activity

Inhibition of a matrix metalloprotease 2 activity was tested using gelatin zymography for the peptides synthesized in Preparation Examples 1. For testing the influence on inhibition of the matrix metalloprotease 2 activity, it is observed that inhibition of the matrix metalloprotease 2 activity by the peptides in case of presence of the matrix metalloprotease 2 and using fibroblasts, respectively.

For observing the influence on direct inhibition of the matrix metalloprotease 2 activity by the peptides, after mixing the peptides and the matrix metalloprotease 2 and incubating for 1 hr at room temperature, the matrix metalloprotease 2 activity was measured by gelatin zymography.

After performing SDS-PAGE with gelatin substrate (2 mg/ml), 2.5% Triton X-100 was treated for 30 min and buffer (50 mM Tris-HCl, 0.2 M NaCl, 5 mM $CaCl_2$, 1% Triton X-100) was treated for 24 hr at 37° C. Gel treated was dyed with Coomassie brilliant blue R250 (Sigma) and decolorizing buffer (5% methanol, 7.5% acetic acid, distilled water) was treated. The matrix metalloprotease 2 activity was shown as band represented by gelatin hydrolysis.

In order to evaluate the peptides whether they have inhibition activities of the matrix metalloprotease 2 activity using fibroblasts, aliquot ($3 \times 10^4$ cells) of fibroblasts was added to each well of 24-well plates and cultured under for 24 hr. After 24-hr culture with the medium not containing serum, cells cultured were collected from bottom of the plates and centrifuged, followed by collecting supernatants. Afterwards the matrix metalloprotease 2 activity was observed.

Figure 4A:
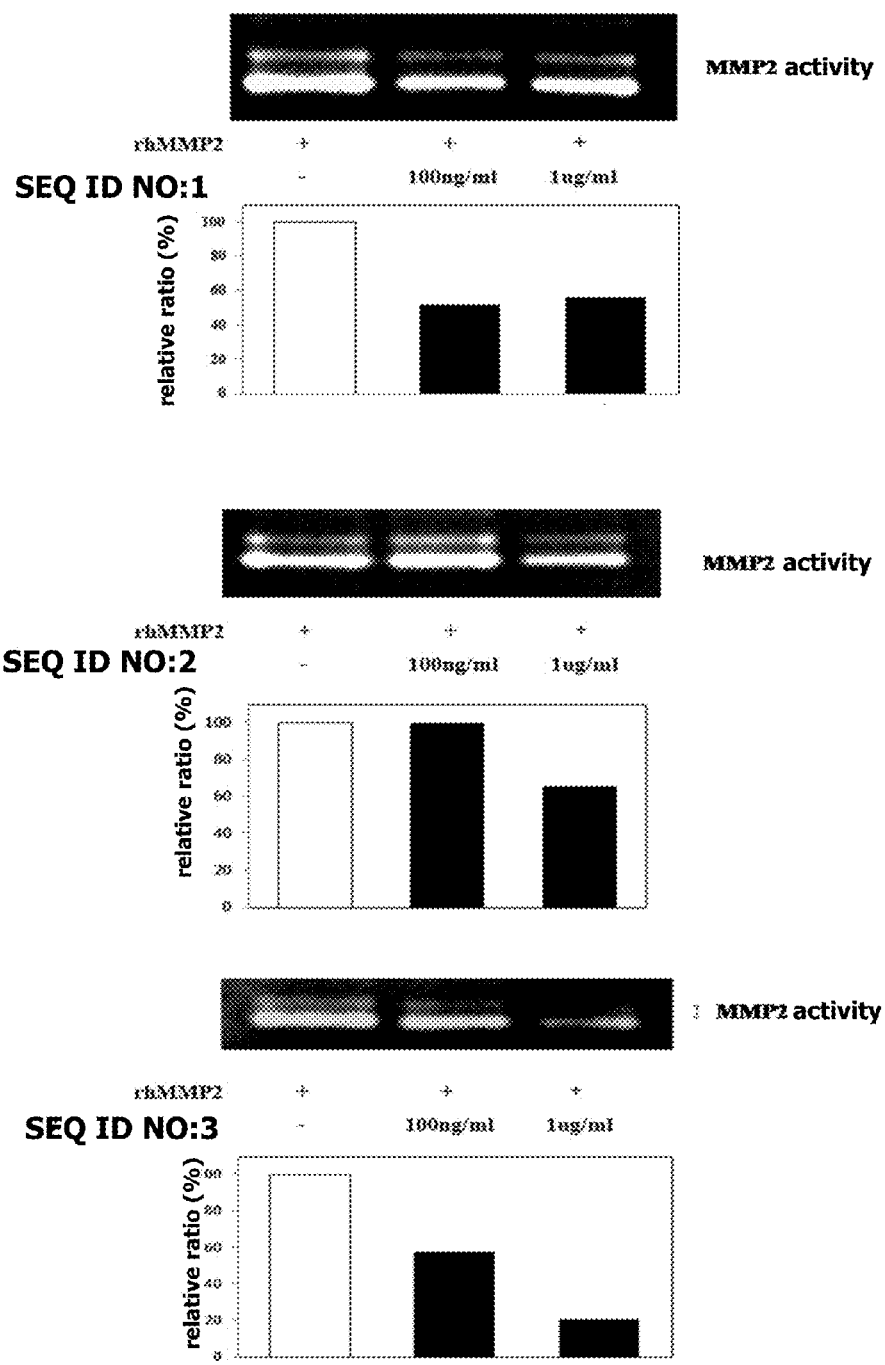
FIG. 4a is a gelatin zymography data demonstrating inhibitory effects on a matrix metalloprotease 2 activity in case of the treatment of the peptides of the present invention by concentration.
Figure 4B:
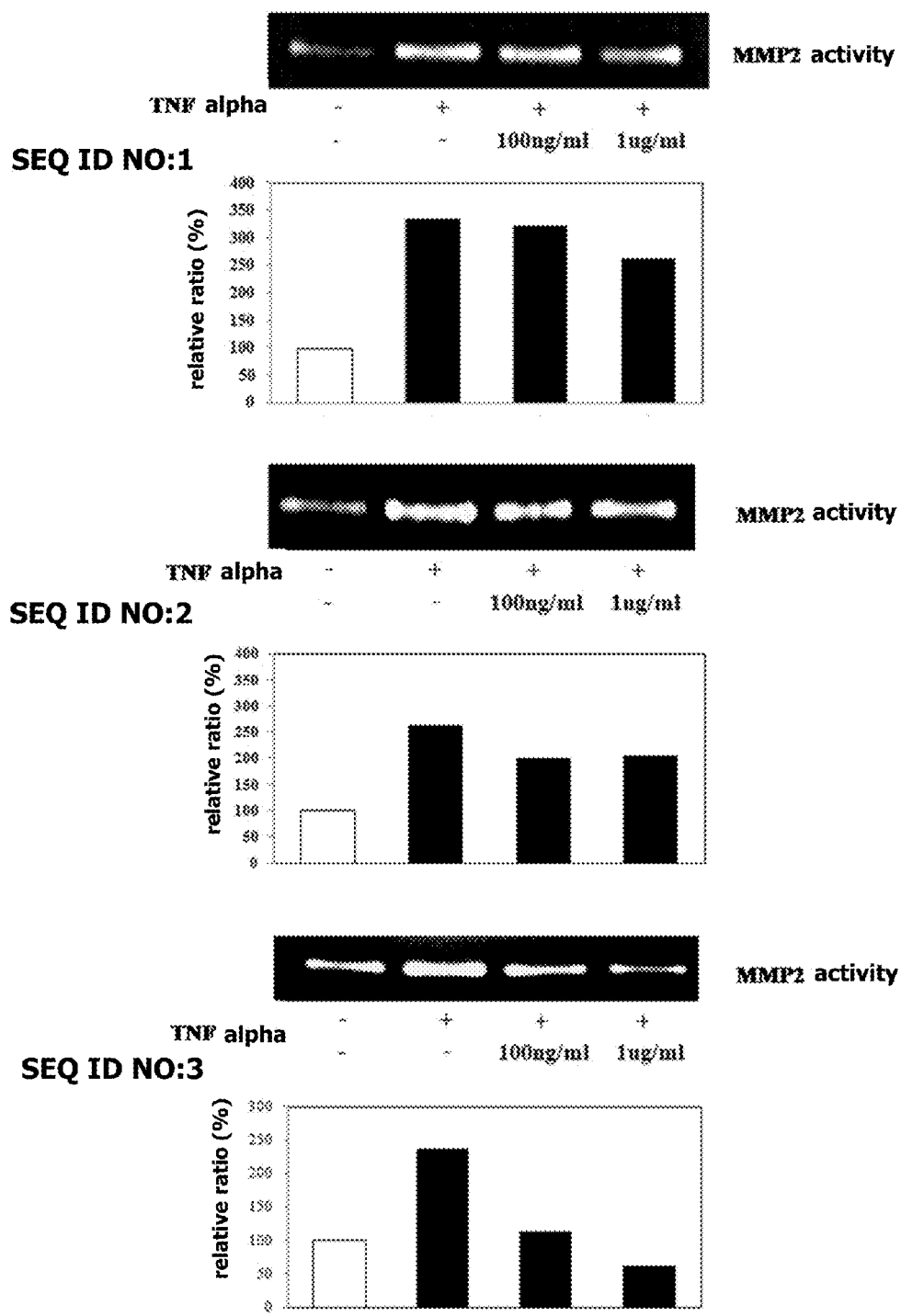
FIG. 4b is a gelatin zymography data demonstrating inhibitory effects on the matrix metalloprotease 2 activity in fibroblasts in case of the treatment of the peptides of the present invention by concentration.
Figure 4C:
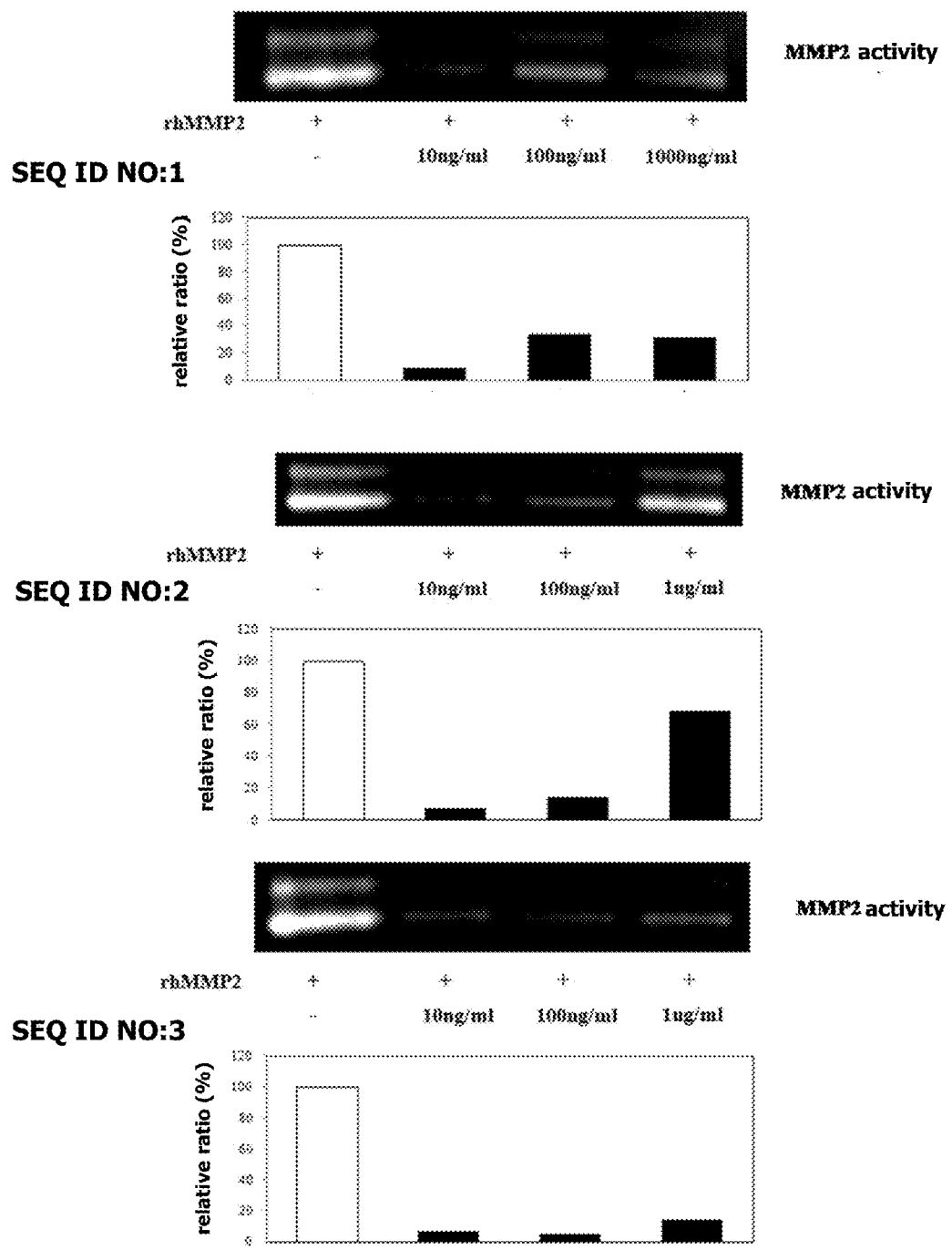
FIG. 4c is a gelatin zymography data demonstrating direct inhibitory effects on the matrix metalloprotease 2 activity in case of the treatment of the peptides of the present invention by concentration.

Consequentially, it is observed that the matrix metalloprotease 2 activity is inhibited by the treatment of the peptides of the present invention by concentration using gelatin zymography (FIGS. 4a and 4c). In addition, the same result is observed in case of usage of the NIH3T3 fibroblasts (FIG. 4b).

Experimental Example 4

Inhibitory Effects of Synthetic Peptides on Collagen Degradation

Human primary dermal fibroblasts cultured in 24-well plates at a density of $3 \times 10^4$ cells/well for 24 hr. After incubating with medium containing 5% serum for 42 hr, the matrix metalloprotease 2 and the peptides were treated for 6 hr. After collecting supernatants by centrifugation, the amount of collagen was determined using collagen kit. In addition, after inducing collagen synthesis artificially with IGF-1(insulin-like growth factor type 1) under the same culture conditions as described above and incubating with the matrix metalloprotease 2 and the peptides for 4 hr, the evaluation whether the peptides have inhibition activities of collagen degradation using collagen kit.

Figure 5A:
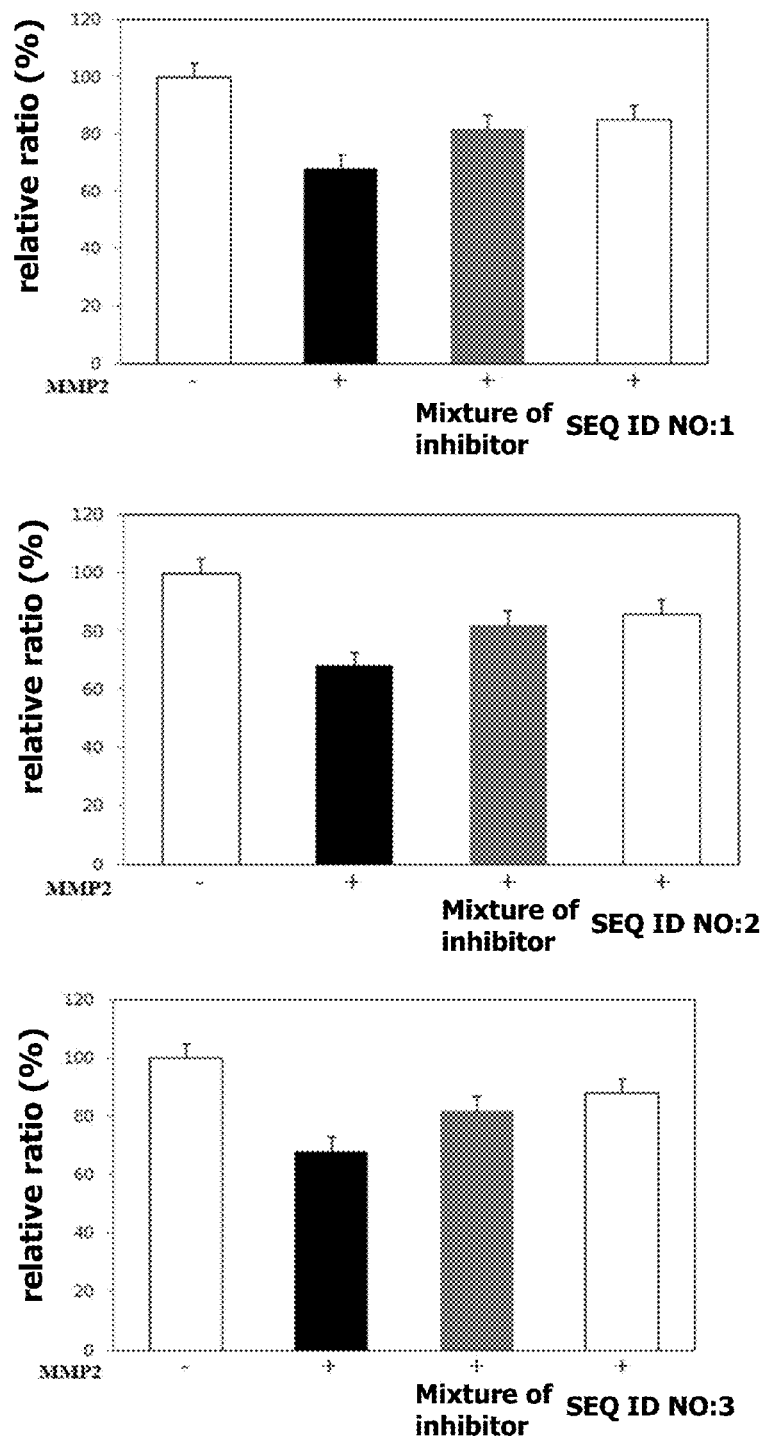
FIG. 5a is a data demonstrating inhibitory effects on collagen degradation in case of the treatment of the peptides of the present invention by concentration after inducing collagen degradation by the matrix metalloprotease 2 (MMP2).
Figure 5B:
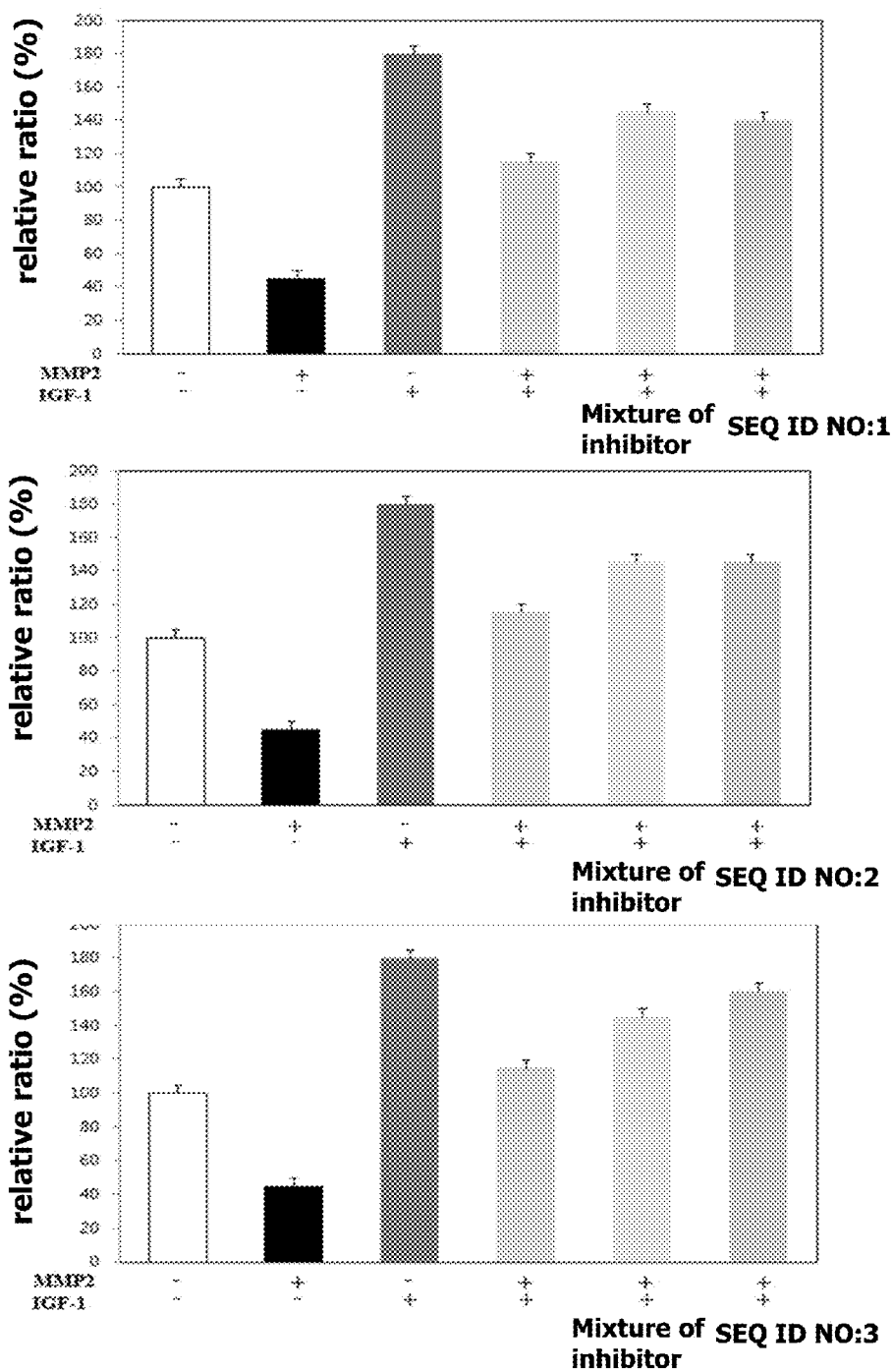
FIG. 5b is a data demonstrating inhibition of collagen degradation in case of the treatment of the peptides of the present invention by concentration after inducing collagen synthesis by IGF-1 and facilitating collagen degradation by the matrix metalloprotease 2 (MMP2).

FIG. 5a represents the result that is performed to evaluate whether the peptides of the present invention have inhibit function of collagen degradation induced by the matrix metalloprotease 2 (MMP2). It reveals that the collagen degradation induced in case of the treatment of the matrix metalloprotease 2 in vivo and inhibited in case of the treatment of the each peptide simultaneously. In addition, after inducing collagen synthesis by IGF-1 treatment, it shows that all three peptides inhibit collagen degradation in case of the treatment of the matrix metalloprotease 2 and the peptides (FIG. 5b)

Experimental Example 5

Figure 6A:
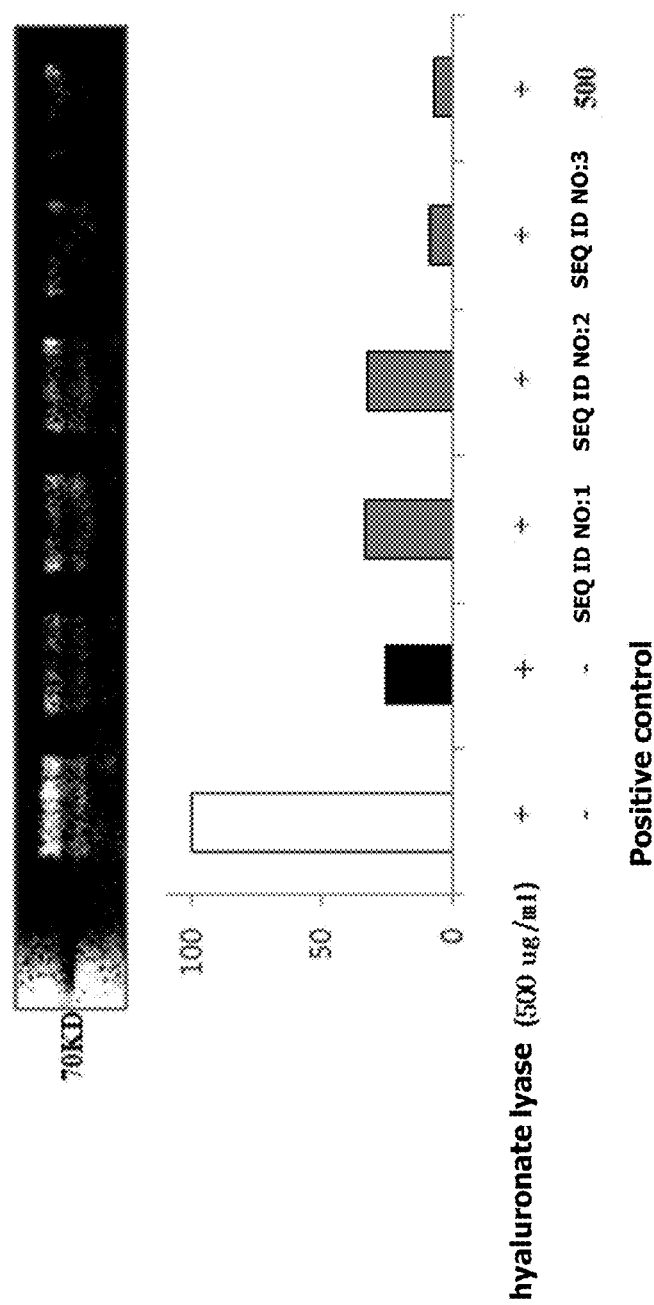
FIG. 6a is a gelatin zymography data demonstrating inhibitory effects on hyaluronic acids degradation in case of the treatment of the peptides of the present invention.
Figure 6B:
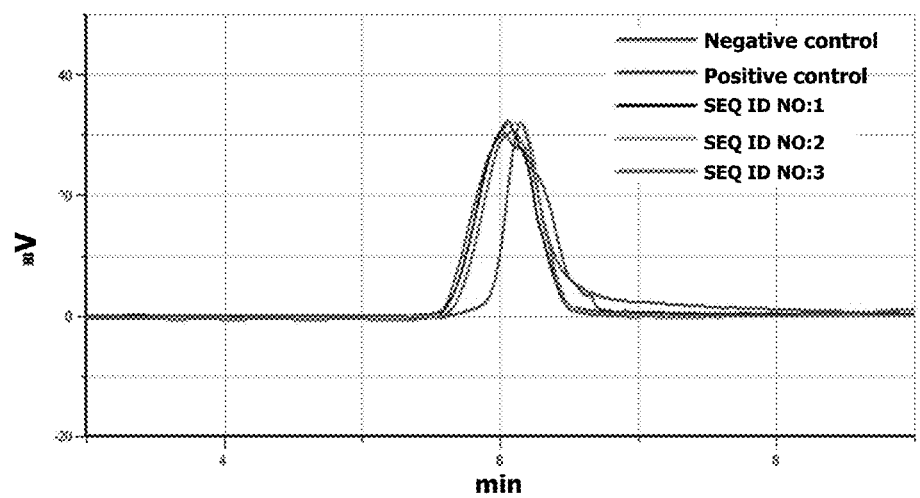
FIG. 6b, c and d represent inhibition of degradation of hyaluronic acids in filler products by time in case of the treatment of the peptides of the present invention by concentration after artificially inducing degradation of hyaluronic acids by addition of Hyaluronate lyase into the filler products.
Figure 6C:
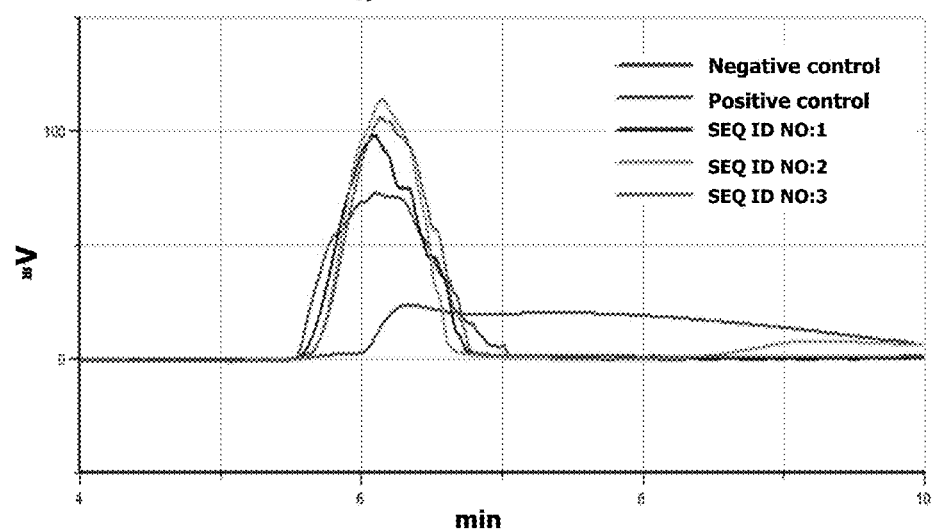
FIG. 6e represents effects on residence times of filler products when the filler product containing hyaluronate lyase and the peptide (SEQ ID NO:2) is injected to rat dorsal skin. The effects were determined at intervals of 1-7 days. As a result, hyaluronic acids degradation effect is excellent and filler products stayed for longer period in case of a sample which is injected with filler products containing the peptide (SEQ ID NO:2) than in case of a sample which is injected with only filler products.
Figure 6D:
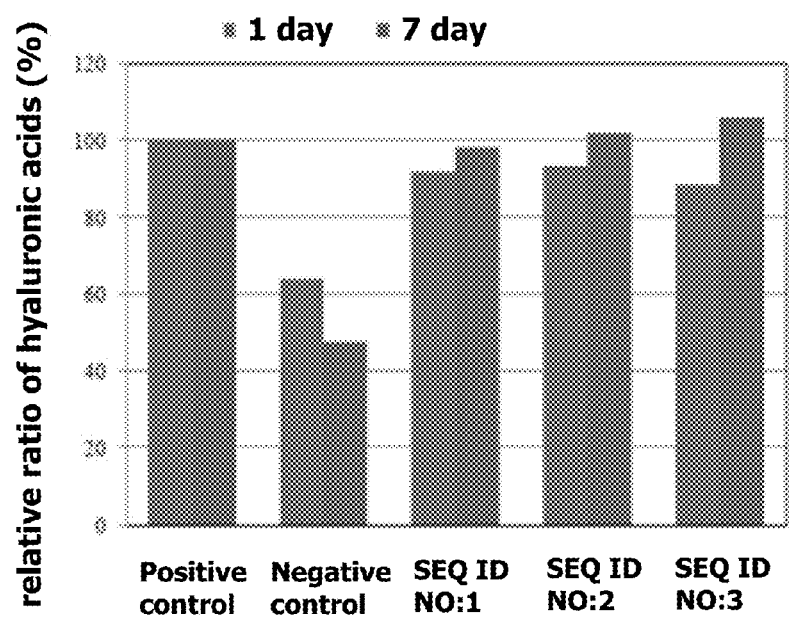
Figure 6E:
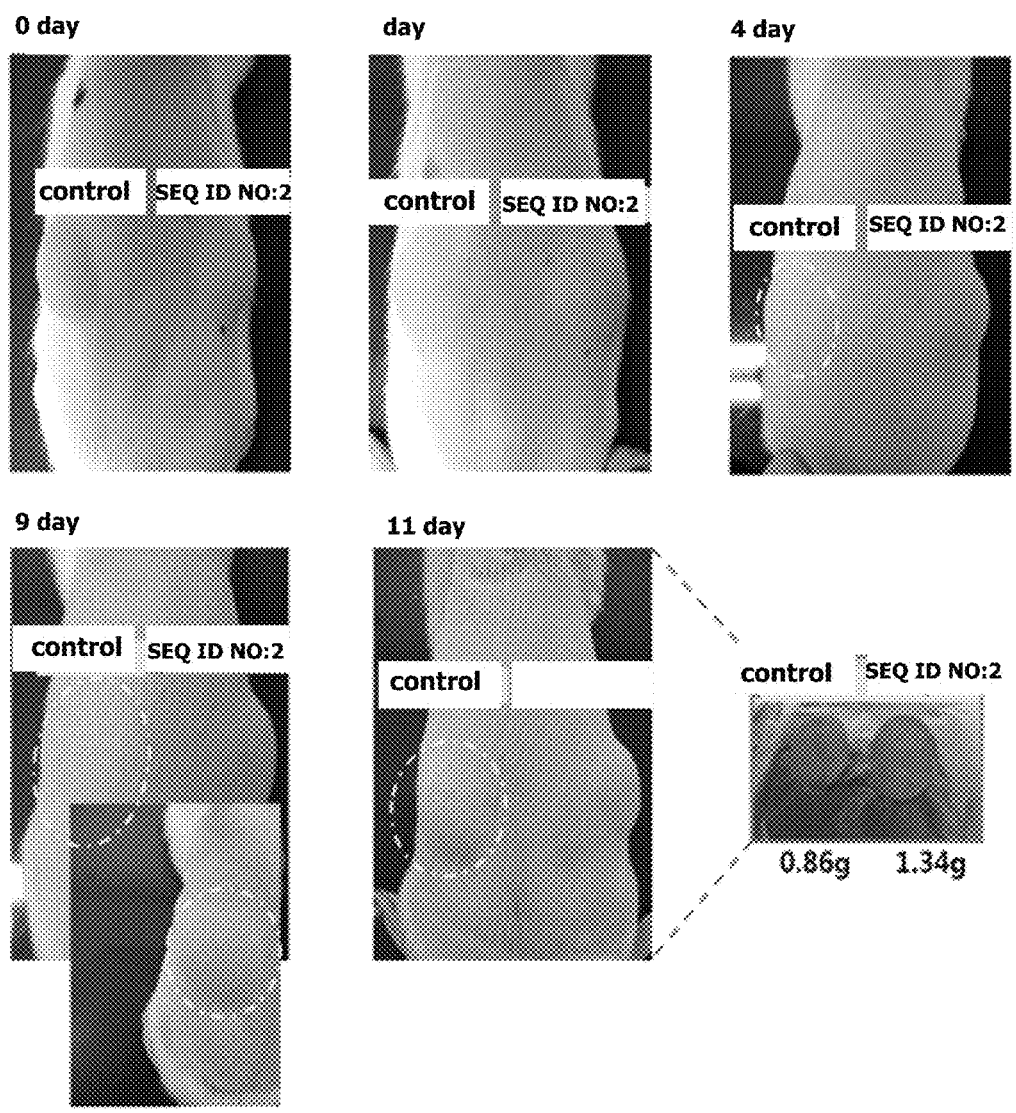

Inhibitory Effects of Synthetic Peptides on Degradation of Hyaluronic Acids in Filler Products Hyaluronate lyase was artificially put into a commercial filler product at a concentration of 100 ug to induce degradation of hyaluronic acids, and then 200 ug peptides were treated. After then, degradation of hyaluronic acids inside the filler product was observed for 7 days (FIGS. 6a and 6b, c, d). An assay using GPC column and an in vivo experiment using rats are performed. Control group was treated with hyaluronate lyase, and treatment group was co-treated hyaluronate lyase and each peptide. When the filler product was injected into rat skin, the degradation of hyaluronic acids inside the filler was inhibited by the treatment of peptides (FIG. 6e).

Experimental Example 6

Inhibitory Effects of Synthetic Peptides on Melanosome Transfer

Phagocytosis assay was performed using HaCaT keratinocyte to investigate inhibitory effects of the synthetic peptides on melanosome transfer. Fluoroscence binding bioparticles are used as materials for phagocytosis. After culturing in 96-well plates at a density of $3 \times 10^3$ cells/well for 24 hr, the HaCaT keratinocyte was cultured in serum-free medium for 6 hr. After treating 1 μg/ml trypsin for induction of phagocytosis, 1 μg/ml peptides were treated for 48 hr. As a result, phagocytosis of bioparticles into the keratinocyte was observed with a fluorescence microscope.

Figure 7A:
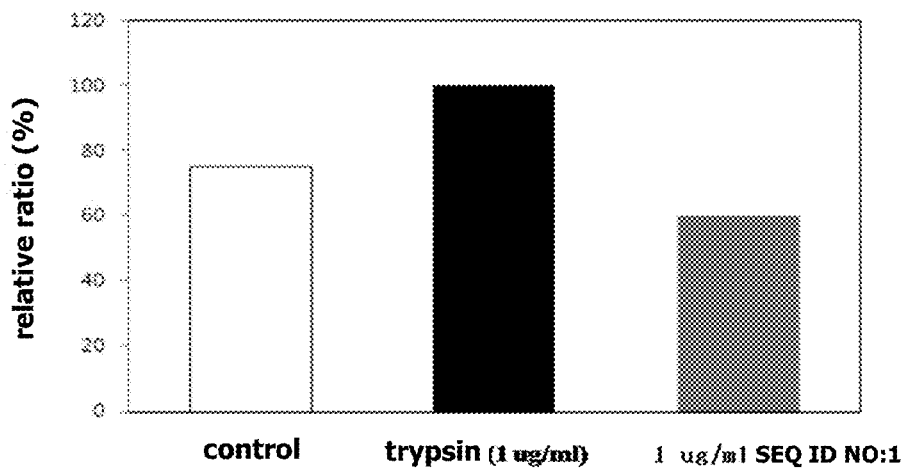
FIG. 7a is a data demonstrating superior effects on skin whitening by melanosome transfer inhibition effects of the peptides of the present invention.
Figure 7A:
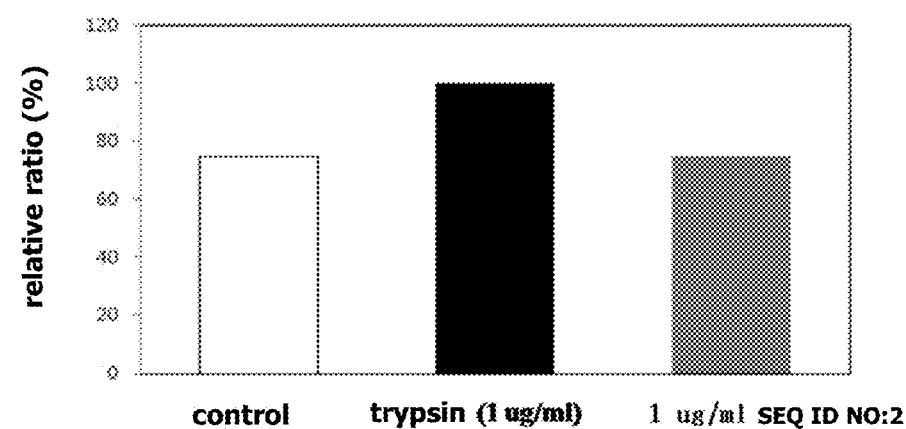
Figure 7A:
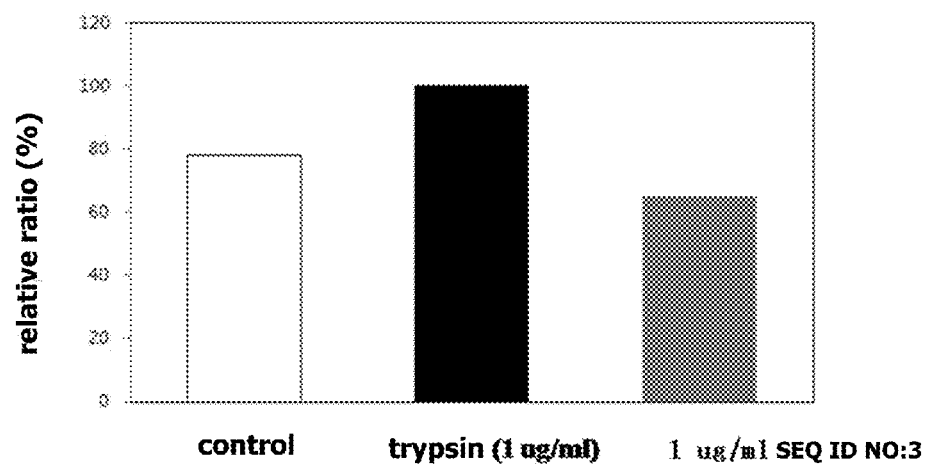
Figure 7B:
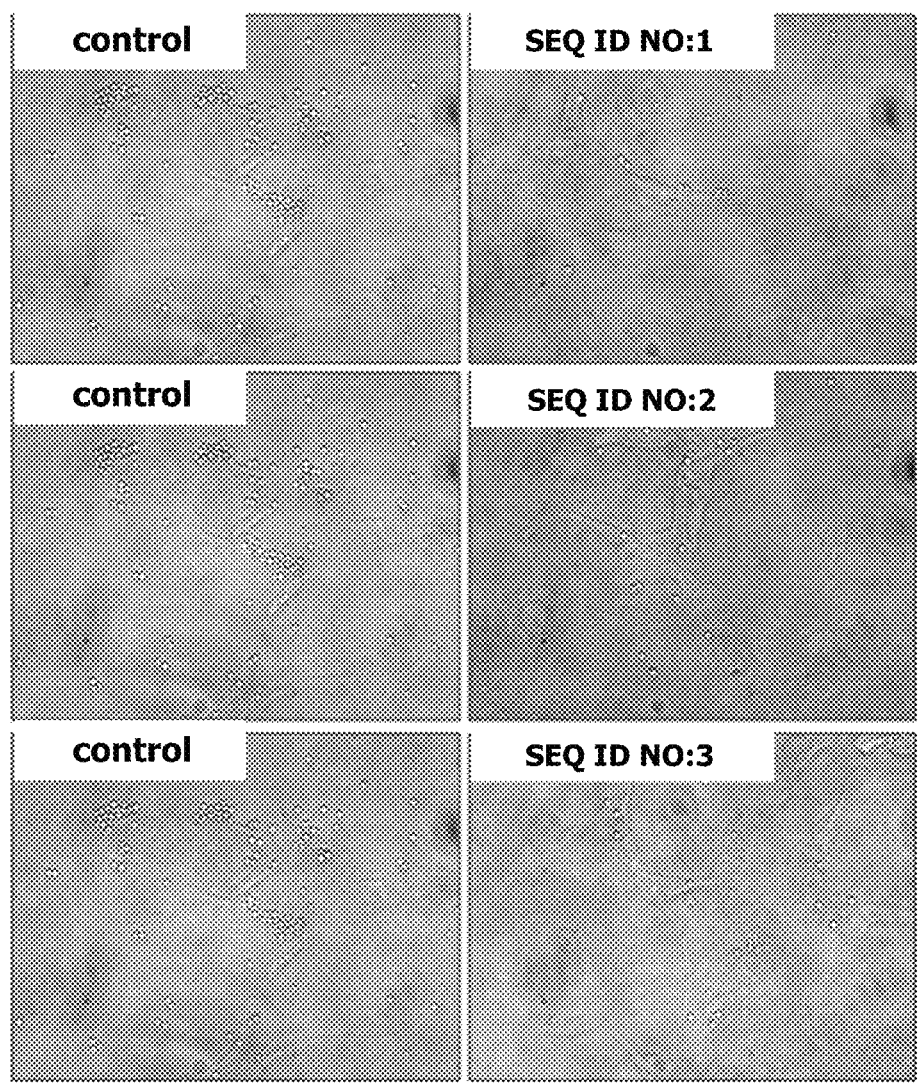
FIG. 7b is a cell shape data demonstrating inhibition effects of the peptides of the present invention on melanosome transfer.

As shown in FIGS. 7a and 7b, the peptides of the present invention inhibit melanosome transfer.

Experimental Example 7

Anti-inflammatory Effects of Synthetic Peptides in Periodontal Cells

An experiment was conducted using human periodontal ligament fibroblast cells (ATCC, USA) to investigate anti-inflammatory effects of the synthetic peptides in periodontal cells having periodontitis.

Human periodontal ligament fibroblast cells were added into a 6-well tissue culture plate ($5 \times 10^1$ cell/well), and cultured for 24 hrs. To induce inflammation in periodontal cells, periodontal cells were treated with LPS (10 μg/ml, Lipopolysaccharide/Sigma, USA), and then were treated with the peptides of the present invention (1 μg/ml). After periodontal cells were cultured for 4 hrs, mRNA was extracted from the cultured cells (control group, LPS-treated group, and LPS and peptide-treated group), and then reverse transcription polymerase chain reaction was conducted using IL-6, IL-1 beta and COX-2 primers. The nucleotide sequences of the used primers were as follows: IL-6 (forward 5'-agaggagacttcacagagga-3', reverse 5'-atctctctgaaggactctgg-3'), IL-1 beta (forward 5'-ccgtggaccttccaggatca-3', reverse 5'-gatccacactctccagctgc-3'), COX-2 (forward 5'-cccccacagt-caaagacact-3', reverse 5'-ccccaaagatagcatctgga-3'), Actin (forward 5'-gatctcaaagacaaccaactagtg-3', reverse 5'-ctccagct-gaagactcctcccag-3').

Figure 8:
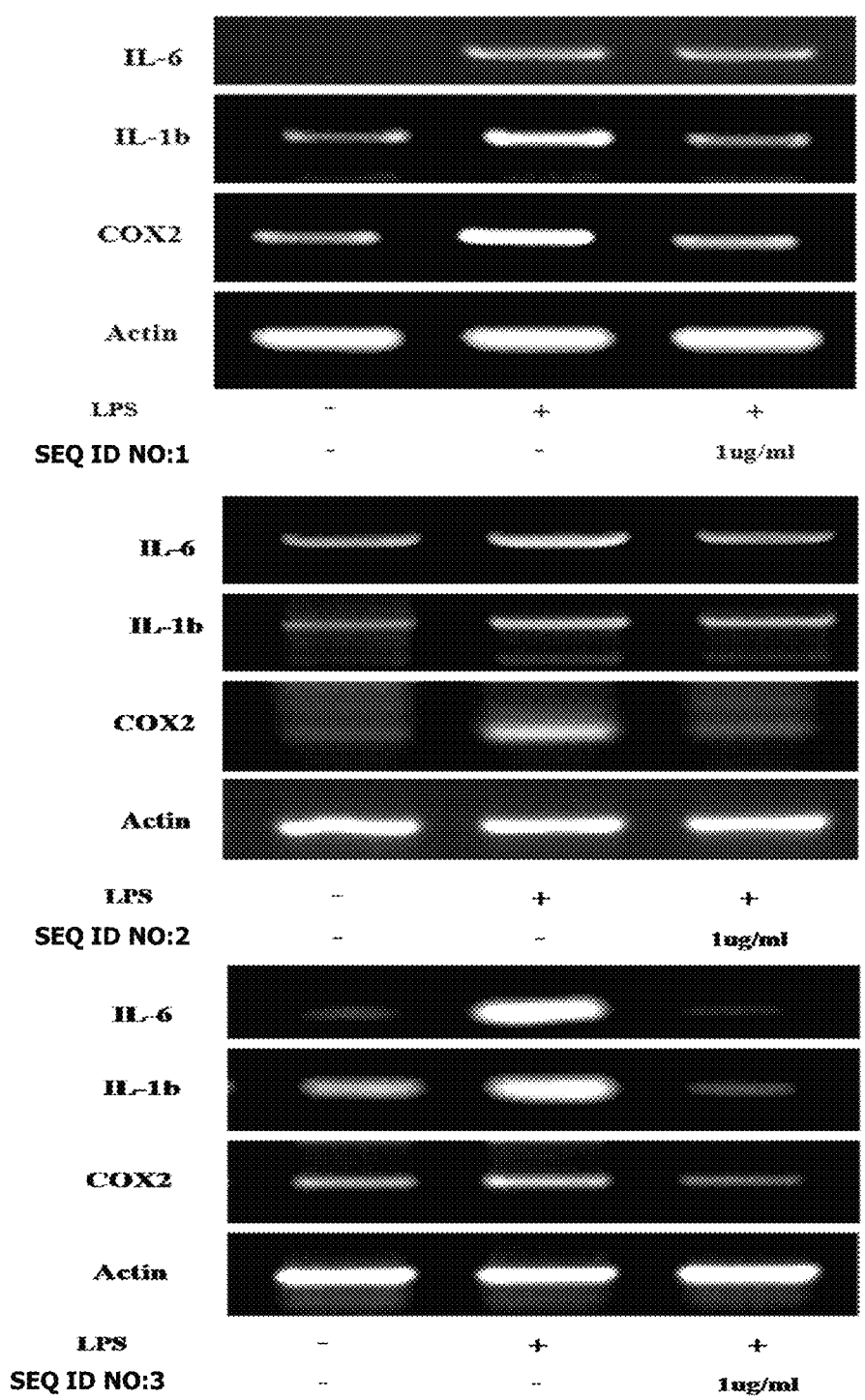
FIG. 8 is a RT-PCT data demonstrating anti-inflammation effects of the peptides of the present invention by inhibition of expression of inflammation-related proteins.

As shown in FIG. 8, when inflammation was induced in human periodontal ligament fibroblast cells, the expression of IL-6, IL-1beta and COX-2 which are an inflammatory cytokine, was increased, whereas the expression of the three inflammatory cytokines was remarkably decreased when the peptides of the present invention were co-treated (FIG. 8).

Experimental Example 8

Inhibitory Effects of Synthetic Peptides on the Formation of Lipid in Adipocytes An experiment was conducted using pre-adipocyte, 3T3-L1 cells (ATCC, USA) to investigate inhibitory effects of the synthetic peptides on adipogenesis. Pre-adipocytes (3T3-L1 cells) at passage 8 were added into a 24-well tissue culture plate ($3 \times 10^4$ cell/well), and cultured for 24 hrs. In control group, Pre-adipocytes were cultured in DMI medium (0.5 mM IBMX, 0.25 μM dexametasone and 1 μg/ml insulin) to differentiate the pre-adipocytes into adipocytes. In treatment group, each peptide at concentration of 1 μg/ml was added DMI medium. After then, the cells were cultured for 10 days to induce differentiation.

Figure 9:
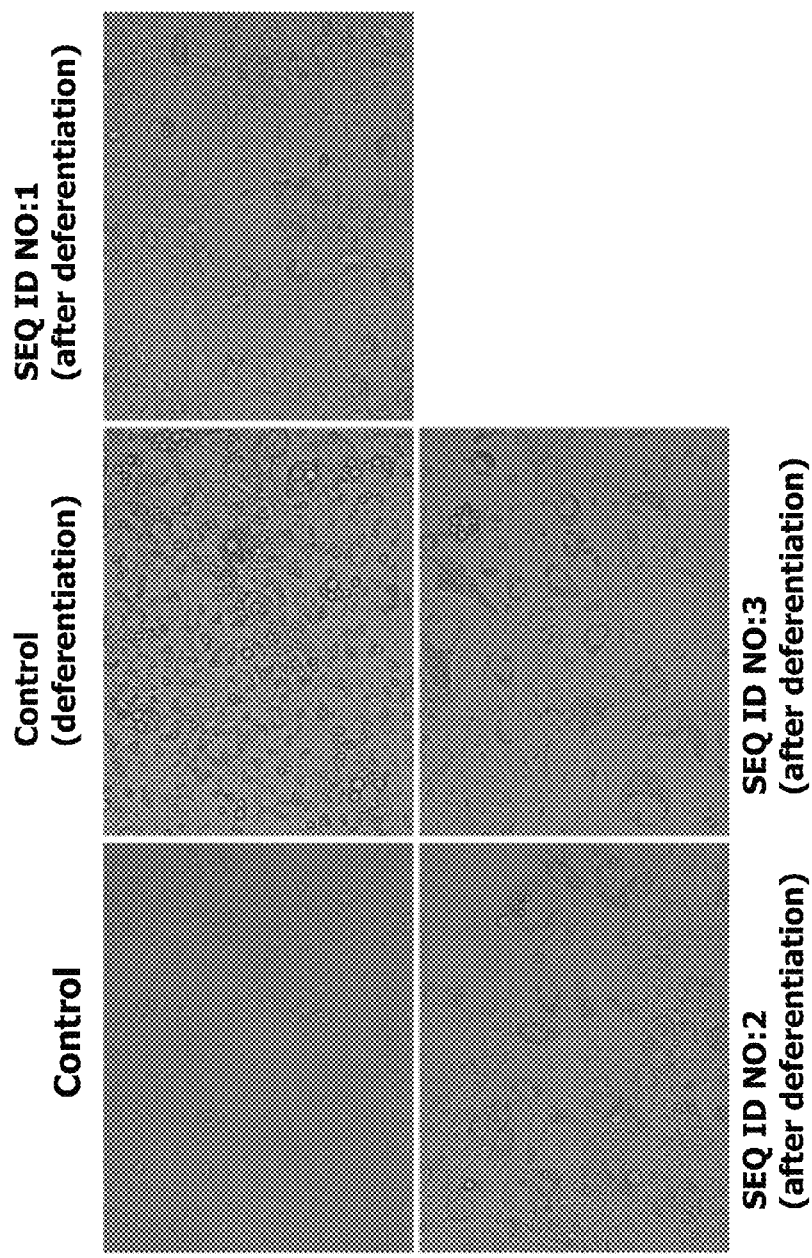
FIG. 9 is a data demonstrating inhibition of adipogenesis in case of the treatment of the peptides of the present invention.

As shown in FIG. 9, as a result of microscope observation, pre-adipocytes in control group were differentiated into adipocytes, and lipid was formed on the cells. On the other hand, the formation of lipid in each peptide-treated group was remarkably decreased as compared with control group.

Experimental Example 9

Inhibitory Effects of Synthetic Peptides on Angiogenesis

Using HUVEC (Human Umbilical Vein Endothelial Cells, ATCC, USA), tube formation was observed to investigate inhibitory effects of the synthetic peptides on angiogenesis.

After matrigel was added into a 96-well tissue culture plate for matrigel solidification (50 μl/well) and maintained at 37° C. for 30 min, HUVECs were cultured in non-growth supplement medium containing 0.2% serum which was added into the solidified matrigel. At this time, HUVECs were treated with each peptide (1 μg/ml), and cultured at 37° C. After 5 hrs, tube formation was observed with an optical microscope.

Figure 10:
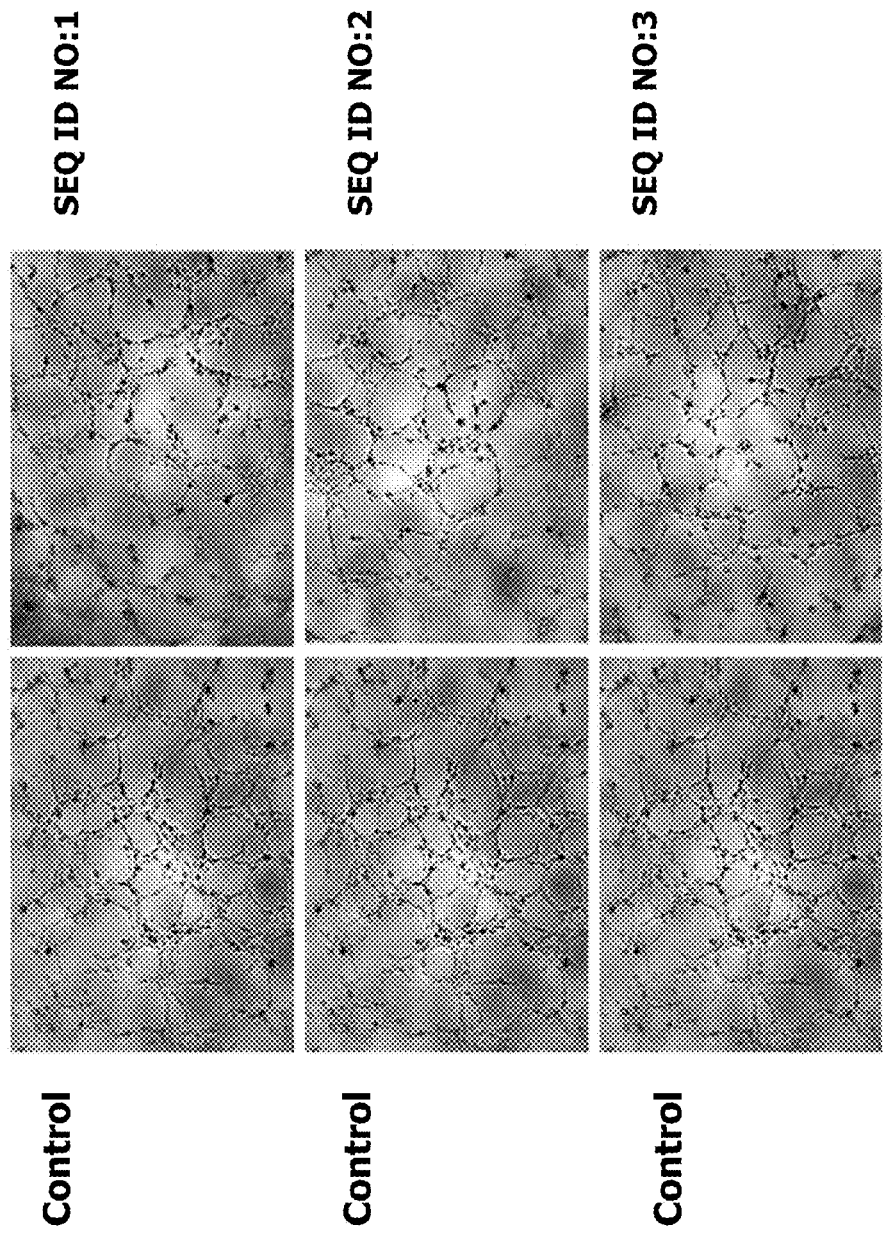
FIG. 10 is a data demonstrating angiogenesis inhibition of HUVEC cells in case of the treatment of the peptides of the present invention.

As shown in FIG. 10, tube formation was inhibited by the treatment of each peptide as compared with control group. This result shows that each synthetic peptide has an inhibitory effect on angiogenesis.

Example 1

Preparation of Nano Peptide 50 mg of the peptide synthesized in Example 1 above was dissolved in 500 ml of distilled water by vigorous agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics in alone or combination with others.

Formulation Example 1

Preparation of Skin Softner

A skin softner containing one or more peptide nanosomes prepared in Example 1 was formulated according to the following composition:

TABLE 2

| Ingredients | Content (wt %) |
|---|---|
| Peptide nanosomes | 0.001 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Preparation of Nutrient Cream

A nutrient cream containing one or more peptide nanosomes prepared in Example 1 was formulated according to the following composition:

TABLE 3

| Ingredients | Content (wt %) |
|---|---|
| Peptide nanosomes | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid containing one or more peptide nanosomes prepared in Example 1 was formulated according to the following composition:

TABLE 4

| Ingredients | Content (wt %) |
|---|---|
| Peptide nanosomes | 0.002 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Preparation of Essence

An essence containing one or more peptide nanosomes prepared in Example 1 was formulated according to the following composition:

TABLE 5

| Ingredients | Content (wt %) |
|---|---|
| Peptide nanosomes | 0.005 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amout |
| Total | 100 |

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A peptide inhibiting a matrix metalloproteinase activity, consisting of an amino acid sequence selected from the group consisting of SEQ ID NOs: 1-3.

2. The peptide according to claim 1, wherein the peptide have facilitation ability of cell growth.

3. The peptide according to claim 1, wherein the peptide inhibits cell death by oxidative stress.

4. The peptide according to claim 1, wherein the peptide inhibits a matrix metalloproteinase (MMP) 2 activity.

5. The peptide according to claim 1, wherein the peptide inhibits degradation of collagen.

6. The peptide according to claim 1, wherein the peptide inhibits degradation of hyaluronic acid.

7. The peptide according to claim 1, wherein the peptide inhibits melanosome transfer.

8. The peptide according to claim 1, wherein the peptide inhibits lipid formation in adipocyte cells.

9. The peptide according to claim 1, wherein the peptide inhibits angiogenesis.

10. A method for improving skin conditions, comprising administering to a subject a composition containing the peptide according to claim 1 as an active ingredient.

11. The method according to claim 10, wherein the improvement of skin conditions is the improvement of wrinkle or skin elasticity, improvement of skin aging, improvement in skin moisture, removal of wound, regeneration of skin or skin whitening.

12. A method for filling a skin, comprising administering to a subject (a) the peptide according to claim 1; and (b) hyaluronic acid.

13. A method for treating obesity, comprising administering to a subject a composition containing the peptide according to claim 1 as an active ingredient.

* * * * *